US008993275B2

(12) United States Patent
Spodsberg

(10) Patent No.: US 8,993,275 B2
(45) Date of Patent: Mar. 31, 2015

(54) POLYPEPTIDES HAVING CELLOBIOHYDROLASE ACTIVITY AND POLYNUCLEOTIDES ENCODING SAME

(71) Applicants: Novozymes A/S, Bagsvaerd (DK); Novozymes Inc., Davis, CA (US)

(72) Inventor: Nikolaj Spodsberg, Bagsvaerd (DK)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 13/765,166

(22) Filed: Feb. 12, 2013

(65) Prior Publication Data

US 2014/0329293 A1 Nov. 6, 2014

(51) Int. Cl.
*C12P 19/14* (2006.01)
*C12N 9/42* (2006.01)

(52) U.S. Cl.
CPC ............... *C12N 9/2437* (2013.01); *C12P 19/14* (2013.01)
USPC ............. 435/99; 435/100; 435/101; 435/105; 435/252.3; 435/254.11; 435/254.2; 435/257.2; 435/320.1; 536/23.2; 536/23.4; 536/23.7; 536/23.74

(58) Field of Classification Search
None
See application file for complete search history.

(56) References Cited

U.S. PATENT DOCUMENTS 6,566,113 B1 * 5/2003 Takayama et al. ............ 435/209
7,220,565 B2 * 5/2007 Brown et al. ................. 435/209
8,124,394 B2 * 2/2012 Maiyuran et al. ............. 435/201
8,354,260 B2 * 1/2013 Imamura et al. .............. 435/183
8,470,592 B2 * 6/2013 Brevnova et al. .......... 435/320.1
2004/0001904 A1 * 1/2004 Gielkens et al. ................ 426/20
2004/0197890 A1 * 10/2004 Lange et al. .................. 435/209
2006/0053514 A1 * 3/2006 Wu et al. ....................... 800/284
2009/0162916 A1 * 6/2009 Adney et al. .................. 435/209
2010/0255542 A1 * 10/2010 Arnold et al. ................... 435/72
2011/0300263 A1 * 12/2011 Koch et al. ....................... 426/61
2012/0260371 A1 * 10/2012 Brown et al. ................. 800/298
2012/0272410 A1 * 10/2012 Vlasenko et al. ............. 800/298
2012/0306879 A1 * 12/2012 Yokoyama .................... 345/428
2013/0052694 A1 * 2/2013 Montalibet et al. ............. 435/99
2013/0061354 A1 * 3/2013 Sagt et al. ..................... 800/306
2013/0189734 A1 * 7/2013 Liu et al. ...................... 435/69.1
2013/0198910 A1 * 8/2013 Spodsberg .................... 800/298
2013/0210087 A1 * 8/2013 Liu et al. ......................... 435/99
2013/0260420 A1 * 10/2013 Morant et al. .............. 435/71.1

FOREIGN PATENT DOCUMENTS

EP 137280 A1 * 4/1985
WO WO 2009108941 A2 * 9/2009
WO WO 2009133035 A1 * 11/2009
WO WO 2009133036 A1 * 11/2009
WO WO 2012101206 A2 * 8/2012
WO WO 2012103288 A1 * 8/2012
WO WO 2012103350 A1 * 8/2012
WO WO2013064097 A1 * 5/2013

* cited by examiner

*Primary Examiner* — Rebecca Prouty
*Assistant Examiner* — Richard Ekstrom
(74) *Attorney, Agent, or Firm* — Eric J. Fechter

(57) ABSTRACT

The present invention relates to isolated polypeptides having cellobiohydrolase activity and polynucleotides encoding the polypeptides. The invention also relates to nucleic acid constructs, vectors, and host cells comprising the polynucleotides as well as methods of producing and using the polypeptides.

20 Claims, No Drawings

POLYPEPTIDES HAVING CELLOBIOHYDROLASE ACTIVITY AND POLYNUCLEOTIDES ENCODING SAME

STATEMENT AS TO RIGHTS TO INVENTIONS MADE UNDER FEDERALLY SPONSORED RESEARCH AND DEVELOPMENT

This invention was made in part with Government support under Cooperative Agreement DE-FC36-08GO18080 awarded by the Department of Energy. The government has certain rights in this invention.

BACKGROUND OF THE INVENTION

1. Field of the Invention

The present invention relates to polypeptides having cellobiohydrolase activity and polynucleotides encoding the polypeptides. The invention also relates to nucleic acid constructs, vectors, and host cells comprising the polynucleotides as well as methods of producing and using the polypeptides.

2. Description of the Related Art

Cellulose is a polymer of glucose linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol. Since glucose is readily fermented to ethanol by a variety of yeasts while cellobiose is not, any cellobiose remaining at the end of the hydrolysis represents a loss of yield of ethanol. More importantly, cellobiose is a potent inhibitor of endoglucanases and cellobiohydrolases. The accumulation of cellobiose during hydrolysis is undesirable for ethanol production.

The present invention provides polypeptides having cellobiohydrolase activity and polynucleotides encoding the polypeptides.

SUMMARY OF THE INVENTION

The present invention relates to isolated polypeptides having cellobiohydrolase activity selected from the group consisting of:

(a) a polypeptide having at least 60% sequence identity to the mature polypeptide of SEQ ID NO: 2, a polypeptide having at least 78% sequence identity to the mature polypeptide of SEQ ID NO: 4, a polypeptide having at least 80% sequence identity to the mature polypeptide of SEQ ID NO: 6, a polypeptide having at least 82% sequence identity to the mature polypeptide of SEQ ID NO: 8, a polypeptide having at least 74% sequence identity to the mature polypeptide of SEQ ID NO: 10, or a polypeptide having at least 75% sequence identity to the mature polypeptide of SEQ ID NO: 12;

(b) a polypeptide encoded by a polynucleotide that hybridizes under low, or medium, or medium-high, or high, or very high stringency conditions with (i) the mature polypeptide coding sequence of SEQ ID NO: 1, SEQ ID NO: 3, SEQ ID NO: 5, SEQ ID NO: 7, SEQ ID NO: 9, or SEQ ID NO: 11, (ii) the cDNA sequence thereof, or (iii) the full-length complement of (i) or (ii);

(c) a polypeptide encoded by a polynucleotide having at least 60% sequence identity to the mature polypeptide coding sequence of SEQ ID NO: 1, SEQ ID NO: 3, SEQ ID NO: 5, SEQ ID NO: 7, SEQ ID NO: 9, or SEQ ID NO: 11; or the cDNA sequence thereof;

(d) a variant of the mature polypeptide of SEQ ID NO: 2, SEQ ID NO: 4, SEQ ID NO: 6, SEQ ID NO: 8, or SEQ ID NO: 10, or SEQ ID NO: 12 comprising a substitution, deletion, and/or insertion at one or more (e.g., several) positions; and (e) a fragment of the polypeptide of (a), (b), (c), or (d) that has cellobiohydrolase activity.

The present invention also relates to isolated polypeptides comprising a catalytic domain selected from the group consisting of:

(a) a catalytic domain having at least 60% sequence identity to the catalytic domain of SEQ ID NO: 2 (for example, amino acids 19 to 465 of SEQ ID NO: 2), SEQ ID NO: 4 (for example, amino acids 19 to 454 of SEQ ID NO: 4), SEQ ID NO: 6 (for example, amino acids 19 to 453 of SEQ ID NO: 6), SEQ ID NO: 8 (for example, amino acids 19 to 458 of SEQ ID NO: 8), SEQ ID NO: 10 (for example, amino acids 19 to 454 of SEQ ID NO: 10), or SEQ ID NO: 12 (for example, amino acids 19 to 454 of SEQ ID NO: 12);

(b) a catalytic domain encoded by a polynucleotide having at least 60% sequence identity to the catalytic domain coding sequence of SEQ ID NO: 1 (for example, nucleotides 55-211, 265-668, and 720-1499 of SEQ ID NO: 1), SEQ ID NO: 3 (for example, nucleotides 55-211, 264-664, and 723-1472 of SEQ ID NO: 3), SEQ ID NO: 5 (for example, nucleotides 55-211, 278-678, and 743-1489 of SEQ ID NO: 5), SEQ ID NO: 7 (for example, nucleotides 55-211, 269-672, and 735-1493 of SEQ ID NO: 7), SEQ ID NO: 9 (for example, nucleotides 55-190, 255-604, 658-729, and 787-1536 of SEQ ID NO: 9), or SEQ ID NO: 11 (for example, nucleotides 55-190, 246-586, 650-721, and 777-1535 of SEQ ID NO: 11);

(c) a variant of a catalytic domain comprising a substitution, deletion, and/or insertion of one or more (several) amino acids of the catalytic domain of SEQ ID NO: 2, SEQ ID NO: 4, SEQ ID NO: 6, SEQ ID NO: 8, SEQ ID NO: 10, or SEQ ID NO: 12; and (d) a fragment of a catalytic domain of (a), (b), or (c), which has cellobiohydrolase activity.

The present invention also relates to isolated polynucleotides encoding the polypeptides of the present invention; nucleic acid constructs; recombinant expression vectors; recombinant host cells comprising the polynucleotides; and methods of producing the polypeptides.

The present invention also relates to processes for degrading a cellulosic material, comprising: treating the cellulosic material with an enzyme composition in the presence of a polypeptide having cellobiohydrolase activity of the present invention. In one aspect, the processes further comprise recovering the degraded or converted cellulosic material.

The present invention also relates to processes of producing a fermentation product, comprising: (a) saccharifying a cellulosic material with an enzyme composition in the presence of a polypeptide having cellobiohydrolase activity of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a polypeptide having cellobiohydrolase activity of the present invention. In one aspect, the fermenting of the cellulosic material produces a fermentation product. In another aspect, the processes further comprise recovering the fermentation product from the fermentation.

The present invention also relates to a polynucleotide encoding a signal peptide comprising or consisting of amino acids 1 to 18 of SEQ ID NO: 2, amino acids 1 to 18 of SEQ ID NO: 4, amino acids 1 to 18 of SEQ ID NO: 6, amino acids 1 to 18 of SEQ ID NO: 8, amino acids 1 to 18 of SEQ ID NO: 10, or amino acids 1 to 18 of SEQ ID NO: 12, which is operably linked to a gene encoding a protein; nucleic acid constructs, expression vectors, and recombinant host cells comprising the polynucleotides; and methods of producing a protein.

Sequences of the Invention

*Hohenbuehelia mastrucata* Strain NN009379 Genomic Nucleotide Sequence (SEQ ID NO: 1)

```
   1 ATGTTTCGCA GTATTACCCT TGTACCGCTC GTCTTCTTTG
     CTATCGTCTA CGGCCAGCAA CCATCCGTGA TCACTCCCGA

  81 ATACCATCCT CCCCTAACAA TCTACAAATG CACTTCAAGC
     GGTGGCTGCC AGTCACAAAC CCGTTCCGTC GTTCTTGACG

 161 CGAGCTGGCG CTGGGCGTAC GAGAAAACGT CCCACGACAT
     CTGTATCTCA GGTTCGGTTG CATTCGTGCA TTGCATAGTG

 241 TTTAATCTCA TTAAGTCGTG GAAGACGGCA ACTGGAACAC
     CCTCGTCTGC ATTAACCCCG TTATCTGCGC GCAGGTTTGC

 321 GCCCTTGATG GCGTTGACTA TTCTGCGACG TACGGCATCA
     CGACGAGCGG CAGCACTCTC ACCCTCCGAT ATGTCACACA

 401 AAGTGGGAGA GGCACGAATG TCGGCTCTCG CGTGTTTCTG
     CTGGAAAACG AGAACGAATA CCAGGCATTC AATCTCAAGA

 481 ATCAAGAATT CGCCTTCGAT GTTGATACAT CGCAGCTCCC
     GTGCGGCCTC AAGGGCTCGC TCTACTTCAC GGAGATGGAC

 561 ACAGATGGGG GCTTGGCCAA GTTCCCGGAC AACGATGCAG
     GGGCGAAATT TGGCACAGGC TATTGCGACG CTCAGTGCCC

 641 GCATGAAGTT AAGTGGCAGA ACGGCGAGGT ACGTCTTTGA
     GATCGAACAC AAAACATCGA GTTTACAATC CTACGGCAGG

 721 CTAACATGTT GGACTGGTTC CCGATTTCGA ATGATGAGAG
     GGCCTGGAGA GGCAAGTACG GCGCCTGCTG TACCCAAATT

 801 GATCTGTGGG AAGCGAACCA ATATTCTGCG GCTTTCACCC
     CGCACCCTTG CGTTGAGAAG GTCCGCTGCG AAAATGTAGT

 881 CGACTGCGGG GATTGGAGCA ACAGATACGA TGGCTACTGC
     GATAAAGATG GCTGTGACTA CAACCCTTAC CGCCTCGGTG

 961 ACCCGAGCTT CCTCGGTCCA GGCAAGGCTG TAGACACGAC
     GCAAAAGATT ACCGTCATCA CGCAATTCAT CACTGACGAC
```

-continued

```
1041 AACACCCCAA ATGGCAATCT CGTGGAGATT CGGCGCATCT
     TTAGGCAAAA CGGGATCATC ATTCAGAACG CCCGGGTCAA

1121 CGTTCCCGGC ATCCCACCGT ACGACTCGAT CACAGACGAC
     TTCTGCAGCA CGCAGAAGAC GGCGTTCAAC GACCAGAACT

1201 ACTTTGCGTC GCTGGGTGGA CTTGGGCAGG TGGGGCATGG
     GATGGATAAT GGCTTGGTAC TAGCGATGAG TCTCCTGGAT

1281 GATCCTGATC GCCAATTGCT TTGGCTCGAC AGCACATATC
     CCCCGGATAG GGATGCTGCT GAGCCAGGCG TTACGCGAGG

1361 AACTTGCGCG ACGGCTTCGG GTAAGCCTGT TGATCTTGAG
     GCTGAATCGC CCAATGCCTC GGTCATGTTC TCCAACATCC

1441 GGTACGGGGA CATTGGATCA ACGTACCCAA TGCCTGGCTC
     CGGATCGACT TGTGCATGTT AA
```

Exons/Introns (in Base Pairs) of SEQ ID NO: 1:

| | |
|---|---|
| Exon 1 | 1-211 bp |
| Intron 1 | 212-264 bp |
| Exon 2 | 265-668 bp |
| Intron 2 | 669-719 bp |
| Exon 3 | 720-1502 bp |

Features (in Base Pairs) of SEQ ID NO: 1:

| | |
|---|---|
| Signal Peptide | 1-54 bp |
| Cellobiohydrolase catalytic site (CBH 1) | 55-211, 265-668,720-1499 bp |
| Stop codon | 1500-1502 bp |

Protein sequence of *Hohenbuehelia mastrucata* Strain NN009379 protein (SEQ ID NO: 2):

```
  1 MFRSITLVPL VFFAIVYGQQ PSVITPEYHP PLTIYKCTSS
    GGCQSQTRSV VLDASWRWAY

 61 EKTSHDICIS DGNWNTLVCI NPVICAQVCA LDGVDYSATY
    GITTSGSTLT LRYVTQSGRG

121 TNVGSRVFLL ENENEYQAFN LKNQEFAFDV DTSQLPCGLK
    GSLYFTEMDT DGGLAKFPDN

181 DAGAKFGTGY CDAQCPHEVK WQNGEANMLD WFPISNDERA
    WRGKYGACCT QIDLWEANQY

241 SAAFTPHPCV EKVRCENVVD CGDWSNRYDG YCDKDGCDYN
    PYRLGDPSFL GPGKAVDTTQ

301 KITVITQFIT DDNTPNGNLV EIRRIFRQNG IIIQNARVNV
    PGIPPYDSIT DDFCSTQKTA

361 FNDQNYFASL GGLGQVGHGM DNGLVLAMSL LDDPDRQLLW
    LDSTYPPDRD AAEPGVTRGT

421 CATASGKPVD LEAESPNASV MFSNIRYGDI GSTYPMPGSG
    STCAC
```

Features of SEQ ID NO: 2 (Amino Acid Positions):

| | |
|---|---|
| Signal Peptide | 1-18 |
| Cellobiohydrolase catalytic site (CBH 1) | 19-465 |

Signal Peptide Sequence of SEQ ID NO: 2:
MFRSITLVPLVFFAIVYG

*Hohenbuehelia mastrucata* Strain NN009379 Genomic Nucleotide Sequence

-continued (SEQ ID NO: 3)

```
   1 ATGTTCCCTG TAGCTACTCT AGTCGCCTTT ATCTTTACTG
     CTGTGGCGCA AGCCCAGCAG ATTGGGACCA ACACACTCGA

  81 AACACATCCA CCTCTCAGCA TTCAATCGTG TACCAAGACA
     GACCGTTGTC AGACTCAACA GAGATCCATC GTGCTTGACG

 161 CCAACTGGCG GTGGCTGCAC AACAACGGCG GTTTCACCAA
     CTGTTATACT GGTATGTTAC GTTCGATCTT CGGTTTGACC

 241 GAGCTTTGCT CACCGTGCCG CAGGGAACAC TTGGGATGCG
     ACGCTCTGTC CGGATCCAGC CACATGTGCC GCCAACTGTG

 321 CGCTGGACGG TGCAGACTAC GCCGGCACTT ATGGCATCAC
     GACAAGCGGC AACGCTTTAT CGTTGAAATT CGTAACTCAG

 401 AGCGCCCAGA AAAACGTCGG CTCACGGGTT TACCTTATGG
     CCGATGAAAC GCACTACCAG ACTTTCAATC TCAAAAACAA

 481 GGAGTTCACC TTCGACATCG ATATGTCACA GCTTCCCTGC
     GGTCTCAACG GCGCGCTGTA CTTCTCTCAG ATGCCCGCAG

 561 ATGGCGGTGT TTCTCAGTTT CCGAGCAACA AAGCTGGGGC
     TAAATACGGT ACTGGCTACT GTGACTCGCA GTGGCTGCAC

 641 GACATCAAGT TCATTAGTGG CGAGGTGAGC CTTCCTTCAA
     TCGAGTAATG GCAAAATACA CGCCTAAAGC GCCCTCGTGC

 721 AGGCTAATAT TCTCGGCTGG ACACCGTCAG CCAGTGACCC
     CAACGCCGGT GCCGGGCAGA TGGGTTCCTG CTGCAACGAG

 801 ATGGATATTT GGGAAGCCAA CTCCAATGCT GCTGCCTTCA
     CTCCTCACCC CTGCACCTCG CAAATTCGTT GCACCTCTCC

 881 AACGCAGTGC GGTGACGGAG ATAACCGTGC TACCGGCGTG
     TGCGACAAGG ACGGTTGTGA CTTCAACTCC TTCCGCATGG

 961 GCGACCAGTC GTTCCTTGGC CCTGGCAAGA CCGTCAACAC
     CAATTCGAAA TTCACCGTCG TCACACAATT CCTCACCGCC

1041 GACAACACCA CCACTGGCAC GCTACGCGAA ATCCGTCGGC
     TCTACGTCCA GAACGGCAAG GTCATCCAGA ACTCCAAAAC

1121 GACTATCCCC GGCATGCAAG CGTTCGACTC GATCACTGAT
     CAGTTCTGTA CGGCCCAGAA GACTGCGTTC GGCGACACGA

1201 ATTCGTTTTC TGCTCACGGA GGTCTCGCTG CCATGGGCTC
     TGCCTTTGAT AAGGGCATGG TCTTGGTTAT GAGCATCTGG

1281 GATGACCACG AAGCCAACAT GCTCTGGCTC GACAGCGACT
     TCCCCACAAC CAAGTCGGCG TCTACTCCGG GTGTTGCTCG

1361 CGGCACATGC GCGACCAATT CCAGTGACCC CGCTACCGTC
     GAGTCGCAAT CGCCGGGCGC GACCGTTGTC TTTTCGAACA

1441 TCAAGTTCGG TGACATTGGC TCCACTTTTT CTTAGTGAAG
     TACGTTCATT GCTTTACATT TAGTTTCGTT TCTGACGGAC

1521 TTGATTAGGC TCAACTCATT GTCCTCGACG GGCCAACGAA
     AAATGGTCCG TT
```

Exons/Introns (in Base Pairs) of SEQ ID NO: 3:

| | |
|---|---|
| Exon 1 | 1-211 bp |
| Intron 1 | 212-263 bp |
| Exon 2 | 264-664 bp |
| Intron 2 | 665-722 bp |
| Exon 3 | 723-1475 bp |

Features (in Base Pairs) of SEQ ID NO: 3:

| | |
|---|---|
| Signal Peptide | 1-54 bp |
| Cellobiohydrolase catalytic site (CBH 1) | 55-211, 264-664, 723-1472 bp |
| Stop codon | 1473-1475 bp |

Protein sequence of *Hohenbuehelia mastrucata* Strain NN009379 protein (SEQ ID NO: 4):

```
   1 MFPVATLVAF IFTAVAQAQQ IGTNTLETHP PLSIQSCTKT
     GGCQTQQRSI VLDANWRWLH

  61 NNGGFTNCYT GNTWDATLCP DPATCAANCA LDGADYAGTY
     GITTSGNALS LKFVTQSAQK

 121 NVGSRVYLMA DETHYQTFNL KNKEFTFDID MSQLPCGLNG
     ALYFSQMPAD GGVSQFPSNK

 181 AGAKYGTGYC DSQCPHDIKF ISGEANILGW TPSASDPNAG
     AGQMGSCCNE MDIWEANSNA

 241 AAFTPHPCTS QIRCTSPTQC GDGDNRATGV CDKDGCDFNS
     FRMGDQSFLG PGKTVNTNSK

 301 FTVVTQFLTA DNTTTGTLRE IRRLYVQNGK VIQNSKTTIP
     GMQAFDSITD QFCTAQKTAF

 361 GDTNSFSAHG GLAAMGSAFD KGMVLVMSIW DDHEANMLWL
     DSDFPTTKSA STPGVARGTC

 421 ATNSGVPATV ESQSPGATVV FSNIKFGDIG STFS
```

Features of SEQ ID NO: 4 (Amino Acid Positions):

| | |
|---|---|
| Signal Peptide | 1-18 |
| Cellobiohydrolase catalytic site (CBH 1) | 19-454 |

Signal Peptide Sequence of SEQ ID NO: 4: MFPVATLVAFIFTAVAQA

*Hohenbuehelia mastrucata* Strain NN009379 Genomic Nucleotide Sequence (SEQ ID NO: 5)

```
   1 ATGTTCCGCG CCGCAGCTCT TTTCGCTTAC ACCCTCCTCG
     CTGTTGTTCG AGCCCAGCAA GTTGGCACGA ACACGGCCGA

  81 GACCCACCCT GCGCTGAGCG TGCAGCAATG CACGGCGGGC
     GGTTCCTGCA CAACCCAGGC GCGCTCCATC GTCCTTGATT

 161 CCAACTGGCG CTGGCTGCAC ACGACCACCG GGTTTACCAA
     CTGCTACACC GGTACTTCAG ACATTTGTCT TTCACTTCTC

 241 CTCCTCCTAT GCTTATGCGT GTAATCCTTT TCTTCAGGCA
     ACACTTGGGA CGCATCTCTG TGCCCAGATG GCGCTACATG

 321 TGCGGCCAAC TGTGCACTCG ATGGTGCGGA CTACTCCGGC
     ACATACGGCA TCAGCACGTC TGGCAACGCC CTTACGCTCA

 401 AGTTCATCAC GCAAAGCCAG CAGAAGAACA TCGGCTCGCG
     CGTCTACCTC CTCGAGTCCG ACTCGTCCTA CCAGATCTTC

 481 AACCTCAAGA ACCAGGAGTT CACCGCTGAC ATCGACATGT
     CTAACCTCCC ATGCGGTCTC AACGGTGCTC TGTACTTCTC

 561 GCAGATGCCC AAGGACGGAG GCATGTCCCA GTTCCCCACC
     AACAAAGCCG GTGCCAAGTA TGGAACTGGT TACTGCGACT

 641 CGCAGTGCCC GCATGACATC AAGTTCATCA ATGGCGAGGT
     GCGCTCAACC TTACTCAAGT CAATAACATG GATTTGCACT

 721 GACTGATGCG AATGTTCGAC AGGCAAACGT TGAGGGCTGG
     GCACCATCCC CCAATGACCC GAATGCGGGC ACGGGCACCT

 801 ACGGATCGTG CTGCCCTGAG ATGGATGTCT GGGAGGCCAA
     CTCCATGGCT GCAGCGTACA CTCCCCACCC GTGCACTGCC

 881 TCAGAGCGTT GTGAGGGCAC CGCGTGCGGT GACGGTGATG
     AGCGCTACGA CGGCGTCTGC GACAAGGACG GCTGCGACTT

 961 CAACTCGTTC CGCATGGGCG ACCAGACCTT CCTCGGCCCT
     GGCATGACCG TCGACACCAA TTCCAAGTTC ACCGTCGTCA
```

-continued

```
1041 CCCAGTTCCT CACCGCTGAC AACACCACCA CCGGCACCCT
     CTCTGAGATC CGTCGCCTCT ACGTCCAGAA CGGCCAGGTC

1121 ATCCAGAACT CCAAGGTCAA CATCCCGGGC ATGGACGCCT
     CCATGGACTC GATCACCGAC GAGTTCTGCT CCGCTCAGAA

1201 GACGGCCTTC GGTGACACCA ACTCGTTCCA GTCCAAGGGT
     GGCCTCGCAG CCATGGGAGA CGCTTTCGAC GCCGGCATGG

1281 TTCTCGTCAT GAGTGTTTGG GACGACCACG CAGTCAACAT
     GCTCTGGCTC GACAGTGACT ACCCGACCGA CAAGGACCCG

1361 TCCGCACCCG GTGTTGCTCG CGGTAACTGT GCGACCACCT
     CTGGCTGCAC GACTGACGTC GAGAGCTCTG CCGCCAGCGC

1441 CTCCGTCACT TTCTCGAACA TCAAGTTCGG TGCCATTGGC
     TCGACCTTTT AA
```

Exons/Introns (in Base Pairs) of SEQ ID NO: 5:

| | | |
|---|---|---|
| Exon 1 | 1-211 | bp |
| Intron 1 | 212-277 | bp |
| Exon 2 | 278-678 | bp |
| Intron 2 | 679-742 | bp |
| Exon 3 | 743-1492 | bp |

Features (in Base Pairs) of SEQ ID NO: 5:

| | | |
|---|---|---|
| Signal Peptide | 1-54 | bp |
| Cellobiohydrolase catalytic site (CBH 1) | 55-211, 278-678, 743-1489 | bp |
| Stop codon | 1490-1492 | bp |

Protein sequence of *Hohenbuehelia mastrucata* Strain NN009379 protein (SEQ ID NO: 6):

```
  1 MFRAAALFAY TLLAVVRAQQ VGTNTAETHP ALSVQQCTAG
    GSCTTQARSI VLDSNWRWLH

 61 TTTGFTNCYT GNTWDASLCP DGATCAANCA LDGADYSGTY
    GISTSGNALT LKFITQSQQK

121 NIGSRVYLLE SDSSYQIFNL KNQEFTFDID MSNLPCGLNG
    ALYFSQMPKD GGMSQFPTNK

181 AGAKYGTGYC DSQCPHDIKF INGEANVEGW APSPNDPNAG
    TGTYGSCCPE MDVWEANSMA

241 AAYTPHPCTA SERCEGTACG DGDERYDGVC DKDGCDFNSF
    RMGDQTFLGP GMTVDTNSKF

301 TVVTQFLTAD NTTTGTLSEI RRLYVQNGQV IQNSKVNIPG
    MDASMDSITD EFCSAQKTAF

361 GDTNSFQSKG GLAAMGDAFD AGMVLVMSVW DDHAVNMLWL
    DSDYPTDKDP SAPGVARGNC

421 ATTSGVPTDV ESSAASASVT FSNIKFGAIG STF
```

Features of SEQ ID NO: 6 (Amino Acid Positions):

| | |
|---|---|
| Signal Peptide | 1-18 |
| Cellobiohydrolase catalytic site (CBH 1) | 19-453 |

Signal Peptide Sequence of SEQ ID NO: 6:
MFRAAALFAYTLLAVVRA

*Hohenbuehelia mastrucata* Strain NN009379 Genomic Nucleotide Sequence

-continued (SEQ ID NO: 7)

```
   1 ATGTTCCGCT CAGTAGCTCT TGTCGCTTTT TCGCTCCTCG
     CTATTGTTCA CGGTCAACAA GTCGGCACGC TGCAGGCTGA

  81 GACACACCCG ACAGTCACCA TCCAGAAATG CACGAAGGGT
     GGTAGTTGCA CTACGCAGCA ACGCTCGATT GTGCTCGACT

 161 CGAATTGGCG GTGGTTACAC ACAACATCTG GCAGCACCAA
     TTGCTACACA GGTACGAGGA GCATCTCTTG TTGTATCTAT

 241 ATGTTTTGAG ACTGATTGCG TTCAATAGGA AACACCTGGG
     ATACTTCTCT GTGCCCCGAC GGTGTCACCT GCGCCAAGAA

 321 TTGTGCTCTC GATGGCGCTG ACTACGCCGG CACTTACGGT
     ATTACGGCTA GCGGCAATGC TGTCACTTTT AAGTTTGTGA

 401 CTCACGGCCC GTACTCCACC AACATCGGTG GACGCGCCTA
     CCTCCTCGAG ACCGACTCCA AGTACCAGAT GTTCAATCTC

 481 AATAACCAAG AGTTCACCTT CGATGTCGAC GTGTCGCAGC
     TGCCCTGTGG TCTGAACGGG GCGCTGTATT TCGTTCAGAT

 561 GGACGCTGAC GGCGGCATGG CGAAGTCCCC GAACAACAAG
     GCCGGCGCTA AATACGGCAC GGGCTACTGC GACTCGCAAT

 641 GCCCGCACGA TATCAAGTTC ATCAACGGAG AGGTAAGTCT
     TTTCGCACTG CACCCATTGG GCATACATTC TCATCTTCTC

 721 CGTCTGTACT ATAGGCCAAC GTTGCTGGTT GGACACCCTC
     TCCCAACGAT GCGAACGCCG GCAAGGGCCA GTACGGCACC

 801 TGTTGCAGCG AGATGGACAT CTGGGAGGCG AACTCCATGG
     CTGCCGCCTA CACTCCGCAC GTCTGCACCG GATCGGGCCT

 881 GACGCGCTGC ACGGGCAACG ATTGCGGTGA TGGCGACAAC
     CGCTACGGCG GCATTTGCGA CAAGGACGGC TGCGACTTCA

 961 ACTCGTTCCG CATGGGCGAC AAGAGCTTCT ACGGCAAGGG
     CATGGCCGTC AACACCAACT CCAAGTTCAC CGTCGTCACC

1041 CAATTCCTCA CTAACAACAA CAGCACCTCG GGCACGCTCT
     CGGAAATCCG TCGCTTGTAC GTGCAGAACG GCAAGGTCAT

1121 CGCAAACTCA AAGACAGCCA TCTCCGGCAT GTCCGCGTAC
     GACTCTGTCA CGGATTCATT CTGCAACGCG CAGAAGACCG

1201 CCTTCGGCGA CACCAACTCG TTCGAGCAGC GCGGCGGCCT
     CAAAGCCATG GGCCAGGCCT TCACCAAGGG CATGACCCTC

1281 GTGATGAGTA TTTGGGACGA CCACGAGGCA AACATGCTCT
     GGCTCGATAG CAACTACCCG CTGACCAAAT CCGCGTCCAC

1361 CCCTGGTGTC GCTCGTGGCA CTTGCGCCAC AACATCCGGC
     AAACCCACTG ATGTCGAGTC TCAGAGCCCG AACGCCCAAG

1441 TCATCTACTC CAACATCAAG TACGGAGATA TCGGTTCGAC
     GTTCCAGGCA TCGTAA
```

Exons/Introns (in Base Pairs) of SEQ ID NO: 7:

| | | |
|---|---|---|
| Exon 1 | 1-211 | bp |
| Intron 1 | 212-268 | bp |
| Exon 2 | 269-672 | bp |
| Intron 2 | 673-734 | bp |
| Exon 3 | 735-1496 | bp |

Features (in Base Pairs) of SEQ ID NO: 7:

| | | |
|---|---|---|
| Signal Peptide | 1-54 | bp |
| Cellobiohydrolase catalytic site (CBH 1) | 55-211, 269-672, 735-1493 | bp |
| Stop codon | 1494-1496 | bp |

Protein sequence of *Hohenbuehelia mastrucata* Strain NN009379 protein (SEQ ID NO: 8):

```
  1 MFRSVALVAF SLLAIVHGQQ VGTLQAETHP TVTIQKCTKG
    GSCTTQQRSI VLDSNWRWLH

 61 TTSGSTNCYT GNTWDTSLCP DGVTCAKNCA LDGADYAGTY
    GITASGNAVT FKFVTHGPYS

121 TNIGGRAYLL ETDSKYQMFN LNNQEFTFDV DVSQLPCGLN
    GALYFVQMDA DGGMAKSPNN

181 KAGAKYGTGY CDSQCPHDIK FINGEANVAG WTPSPNDANA
    GKGQYGTCCS EMDIWEANSM

241 AAAYTPHVCT GSGLTRCTGN DCGDGDNRYG GICDKDGCDF
    NSFRMGDKSF YGKGMAVNTN

301 SKFTVVTQFL TNNNSTSGTL SEIRRLYVQN GKVIANSKTA
    ISGMSAYDSV TDSFCNAQKT

361 AFGDTNSFEQ RGGLKAMGQA FTKGMTLVMS IWDDHEANML
    WLDSNYPLTK SASTPGVARG

421 TCATTSGKPT DVESQSPNAQ VIYSNIKYGD IGSTFQAS
```

Features of SEQ ID NO: 8 (Amino Acid Positions):

| | |
|---|---|
| Signal Peptide | 1-18 |
| Cellobiohydrolase catalytic site (CBH 1) | 19-458 |

Signal Peptide Sequence of SEQ ID NO: 8: MFRSVALVAFSLLAIVHG

*Hohenbuehelia mastrucata* Strain NN009379 Genomic Nucleotide Sequence (SEQ ID NO: 9)

```
   1 ATGTTCCGCT CCGCTGCTCT CATTGCTTTC ACCTTCGCGG
     CTGTCGTCCT CGGTCAACAG GTCGGCACCT TGACGGCAGA

  81 GAACCACCCT TCTCTCCAGG TCTCTCAGTG CACCAAGTCT
     GGCGGTTGCA CGACCACCAC TAAGTCCGTC GTGCTTGACG

 161 CCAACTGGCG CTGGCTCCAC AGCACCTCCG GTACGTTTTC
     TGTCACACCA ATTTCTGGTG AGCCGCTAAA ATGACCAAAT

 241 TACAATTTCT ACAGGCTCGA ACAACTGCTA CACCGGTAAC
     ACCTGGGACG CCACCCTGTG CCCCGACGCC GCCACTTGCG

 321 CCACTAACTG TGCGCTCGAT GGTGCCGACT ACTCTGGCAC
     ATACGGAATC ACCACTTCCG GCAACGCGTT GACCATGAAG

 401 TTCGTCACTC AAAGCGCCCA GAAGAACATC GGTTCCCGTG
     TCTACCTTAT GGATGACGCC AGCACATACA AGATGTTCAA

 481 CCTCAAGAAC CAGGAGTTCA CCTTCGACGT CGACATGTCC
     GGGCTTCCCT GCGGACTTAA CGGTGCTTTG TACTTCTCTG

 561 AGATGGCGAA GGATGGTGGC ATGTCGACTC AGCCATCCAA
     CAAGGTACGA ACCCCTGAAG AATACGACAC AATGCCATTC

 641 TGATATTGCT CCCTCAGGCT GGCGCCAAAT ACGGAACTGG
     ATACTGTGAC TCGCAGTGCC CCCACGACAT CAAGTTCATT

 721 GGTGGCAAGG TTAGTAGACC GTTTTCCTGA TTGCGGGGCA
     CCGATCCTCA TGAAATGTTT CTCTAGGCCA ACGTCGCGGG

 801 CTGGGAAGGA TCCCCCAACG ACCCCAACGC CGGCAGTGGT
     ACCATGGGTG CCTGCTGCTC CGAGATGGAC ATCTGGGAGG

 881 CCAACACCAT GGCTGCTGCC TACACCCCCC ACCCTTGCAC
     GACCACTGGT CTCCTCGCCT GCACTGGCAC CCAGTGCGGT

 961 GACGACGACG ACCGTTACAA CGGTGTCTGC GACAAGGACG
     GTTGTGACTT CAACTCGTTC CGCATGGGCG ACAAGACTTT
```

-continued

```
1041 CCTCGGCAAG GGTAAGACTG TCGACACCAC CAAGAAGATC
     ACCGTCGTCA CTCAGTTCAT CACCTCTGAC GGCACTGCCA

1121 ACGGCGACCT CACTGAGATC CGCCGTCTTT ACGTCCAGAA
     CGGCAAGGTC ATCCAAAACA GCATGTCGAG CATCCCAGGC

1201 ACCACGGCCG TCAACTCGCT CACTGACGCG TCCTGCACTG
     CTCAGAAGTC CGTTTTCGGT GACACGAACT CGTTCTCGTC

1281 CAAGGGTGGA ATGAAGGCGA TGGGCGACTC CTTCCAGCGC
     GGCATGGTCC TCGTCATGTC TATCTGGGAC GACCACGCTG

1361 TCAACATGCT CTGGCTCGAC TCCGACTACC CCACCGACGC
     TGACCCCAGC AGCCCCGGTG TCGCTCGCGG AGAGTGTGCC

1441 ACCACCTCCG GCAAGCCCAC CGACGTTGAG GCCAACCCTG
     CGGGCATCCA AGTCATCTAC TCCAACATCA AGTTCGGTGA

1521 CATTGGCTCG ACCTACACTG GCACCGCAGG CGGCAGTCCG
     AGCGGCCCGA GCTCCACCAC TGGCCCCAGC AGCACCGCTG

1601 CCCCGCCCAC GAACACCGCT ACTGCTGGCC TCTACGCCCA
     GTGCGGTGGA ATTGGCTTCA GCGGCCCGAC TGCCTGCGTG

1681 TCTGGCGCGA CCTGCACGAA GCTCAACGAC TGTGCGTTTA
     TTTTGTAACC CTCATGCGCC TTGTCGATAC TGACATTCCC

1761 TTGTAGACTA CTCTCAGTGC CTCCCCTAA
```

Exons/Introns (in Base Pairs) of SEQ ID NO: 9:

| | |
|---|---|
| Exon 1 | 1-190 bp |
| Intron 1 | 191-254 bp |
| Exon 2 | 255-604 bp |
| Intron 2 | 605-657 bp |
| Exon 3 | 658-729 bp |
| Intron 3 | 730-786 bp |
| Exon 4 | 787-1711 bp |
| Intron 4 | 1712-1766 bp |
| Exon 5 | 1767-1789 bp |

Features (in Base Pairs) of SEQ ID NO: 9:

| | |
|---|---|
| Signal Peptide | 1-54 bp |
| Cellobiohydrolase catalytic site (CBH 1) | 55-190, 255-604, 658-729, 787-1536 bp |
| Linker | 1537-1620 bp |
| Cellulose Binding Module (CBM 1) | 1621-1711, 1767-1786 bp |
| Stop codon | 1787-1789 bp |

Protein sequence of *Hohenbuehelia mastrucata* Strain NN009379 protein (SEQ ID NO: 10):

```
  1 MFRSAALIAF TFAAVVLGQQ VGTLTAENHP SLQVSQCTKS
    GGCTTTTKSV VLDANWRWLH

 61 STSGSNNCYT GNTWDATLCP DAATCATNCA LDGADYSGTY
    GITTSGNALT MKFVTQSAQK

121 NIGSRVYLMD DASTYKMFNL KNQEFTFDVD MSGLPCGLNG
    ALYFSEMAKD GGMSTQPSNK

181 AGAKYGTGYC DSQCPHDIKF IGGKANVAGW EGSPNDPNAG
    SGTMGACCSE MDIWEANTMA

241 AAYTPHPCTT TGLLACTGTQ CGDDDDRYNG VCDKDGCDFN
    SFRMGDKTFL GKGKTVDTTK

301 KITVVTQFIT SDGTANGDLT EIRRLYVQNG KVIQNSMSSI
    PGTTAVNSLT DASCTAQKSV

361 FGDTNSFSSK GGMKAMGDSF QRGMVLVMSI WDDHAVNMLW
    LDSDYPTDAD PSSPGVARGE
```

-continued

```
421  CATTSGKPTD VEANPAGIQV IYSNIKFGDI GSTYTGTAGG
     SPSGPSSTTG PSSTAAPPTN

481  TATAGLYAQC GGIGFSGPTA CVSGATCTKL NDYYSQCLP
```

Features of SEQ ID NO: 10 (Amino Acid Positions):

| | |
|---|---|
| Signal Peptide | 1-18 |
| Cellobiohydrolase catalytic site (CBH 1) | 19-454 |
| Linker | 455-482 |
| Cellulose Binding Module (CBM 1) | 483-519 |

Signal Peptide Sequence of SEQ ID NO: 10: MFRSAALIAFTFAAVVLG

*Hohenbuehelia mastrucata* Strain NN009379 Genomic Nucleotide Sequence (SEQ ID NO: 11)

```
   1 ATGTTCCCCG CTTCAGCCCT AATTGCCCTC ACCTTCACCG
     CTGTTGCCTT TGGCCAGCAG GTCGGCACCT TGACACCTGA

  81 GACCCACCCG AAACTCACTG TCTCCAACTG CTCAGCCGGT
     GGCTCGTGCA CAACCAGTCA ACAGTCCATC GTTCTCGATT

 161 CCAACTGGCG CTGGCTCCAT TCGACCAGCG GTATGCACGT
     TGAAACGTCG ATTGTTGTTT CTTTACTAAT TCTATCCGAT

 241 TTTAGGTTCG ACCAACTGCT ACACTGGCAA CACCTGGGAC
     GCCACCCTTT GCCCGAACCC GACAACCTGT GCGACCAACT

 321 GCGCTCTTGA TGGCGCGGAC TACTCTGGCA CCTACGGTAT
     CACCACTTCC GGCAATGCGC TCACCCTTAA ATTCGTCACC

 401 GGGAAGAACG TTGGCTCTCG TGTCTACCTT CTCGACAGCA
     CGGACAACAC GTACCAGTTG TTCAAGCTGA AGAACAAGGA

 481 GTTCACGTTC GACGTCGACA TGTCGAACCT TCCCTGCGGT
     CTCAACGGTG CCCTTTACTT TTCCGAGATG GCTGCCAATG

 561 GCGGTCTCAA CGTTGGCAAC AACAAGGTTT GTTCTCGATT
     TATAAAATAG ACTGTTGTTG CAAGGTCCTG ACGAGCTTTC

 641 GCATTCCAGG CTGGTGCCAA GTACGGAACT GGCTACTGCG
     ACGCTCAGTG CCCGCACGAC ATCAAGTTCA TCAATGGCGA

 721 GGTATGTAGC TTCGAGAATG TAGCAATTAT GTCCTCAGCT
     CACAATTACC CTCCAGGCCA ACGTCATTAA CTGGGCTGGA

 801 TCGCCGAACG ACGTCAACGC CGGCAGTGGC AAGTACGGAG
     CCTGCTGCGA CGAGATGGAC GTCTGGGAGG CCAATAACAT

 881 GGCGAGCGCG TATACTCCTC ACCCGTGCTC GAGCACTGGC
     TTGACCCGTT GCTCCGACGA CGACGCTACC AACAAGTGTG

 961 GTGACGGCTC GAATCGCTAC TCGAGTATCT GCGACAAGGA
     CGGCTGCGAC TTCAACTCGT TCCGCATGGG CGACAAGAAC

1041 TACTCTGGCA AGGGTAAGAC GATTGACACT ACCAAGAAGA
     TTACCGTCGT CACACAGTTC ATCACCGCCG ACGGCACCGA

1121 CACTGGTGCG CTCTCGGAGA TCCGTCGCAT CTACCTCCAG
     AACGGTGTCG TGTACCAGAA CAGCCAGTCG ACGTACTCGA

1201 CCGTCCCTGG CAACTCGATC ACCGACGCGT TCTGCGACGC
     GCAGAAGACG GCGTTCGGAG ACCAGAACCG GTTCAAAGCC

1281 CTCGGCGGCA TCAAGGCTAT GGGCGACTCG ATGGCCAACG
     GCATGGTTCT TGTCATGTCG ATCTGGGACG ACCATGAGGC

1361 GAAGATGCTC TGGCTGGACT CCAACTACCC GCTTGACAAG
     CCTGCGACGA GCCCTGGTGT TGCTCGCGGC GAGTGCGCGA

1441 CCACCTCCGG CGAGCCCACC GACGTAGAGT CGCAGGTTCC
     GAACTCGTCG GTGACGTTCT CGAATATCAA GTTCGGCCCC

1521 ATCGGTAGCA CATACAGCGG CACGACGGGC ACCCCGAGTA
     GCGGCAGCTC CTCCGTCATC CCGCCCAGCA GCTCGGTCTC

1601 TACATCGAGC GCCCCTTCGC AGACCGGCAC GGTTGCTCAC
     TGGGGCCAAT GCGGAGGTAA GTTGTTCAAA TGCTGTTCAT

1681 AAATTGGCTT GGTCTCAGTC TAATTGTTGT CGGATTCAAG
     GCATTGGCTA TACTGGCCCG ACCACCTGCG TGGCTCCCTA

1761 CACTTGCCAA GTCGGCAACC CTTGTACGTG GTCTCCCCTC
     TTGATGATGA TGCCACTACT GAAGAGAACG TCGTCTCCCA

1841 AGACTACTCT CAGTGCCTCT AA
```

Exons/Introns (in Base Pairs) of SEQ ID NO: 11:

| | |
|---|---|
| Exon 1 | 1-190 bp |
| Intron 1 | 191-245 bp |
| Exon 2 | 246-586 bp |
| Intron 2 | 587-649 bp |
| Exon 3 | 650-721 bp |
| Intron 3 | 722-776 bp |
| Exon 4 | 777-1656 bp |
| Intron 4 | 1657-1720 bp |
| Exon 5 | 1721-1783 bp |
| Intron 5 | 1784-1842 bp |
| Exon 6 | 1843-1862 bp |

Features (in Base Pairs) of SEQ ID NO: 11:

| | |
|---|---|
| Signal Peptide | 1-54 bp |
| Cellobiohydrolase catalytic site (CBH 1) | 55-190, 246-586, 650-721, 777-1535 bp |
| Linker | 1536-1631 bp |
| Cellulose Binding Module (CBM 1) | 1632-1656, 1721-1783, 1843-1859 bp |
| Stop codon | 1860-1862 bp |

Protein sequence of *Hohenbuehelia mastrucata* Strain NN009379 protein (SEQ ID NO: 12):

```
  1 MFPASALIAL TFTAVAFGQQ VGTLTPETHP KLTVSNCSAG
    GSCTTSQQSI VLDSNWRWLH

 61 STSGSTNCYT GNTWDATLCP NPTTCATNCA LDGADYSGTY
    GITTSGNALT LKFVTGKNVG

121 SRVYLLDSTD NTYQLFKLKN KEFTFDVDMS NLPCGLNGAL
    YFSEMAANGG LNVGNNKAGA

181 KYGTGYCDAQ CPHDIKFING EANVINWAGS PNDVNAGSGK
    YGACCDEMDV WEANNMASAY

241 TPHPCSSTGL TRCSDDDATN KCGDGSNRYS SICDKDGCDF
    NSFRMGDKNF FGKGKTIDTT

301 KKITVVTQFI TADGTDTGAL SEIRRIYLQN GVVYQNSQST
    YSTVPGNSIT DAFCDAQKTA

361 FGDQNRFKAL GGIKAMGDSM ANGMVLVMSI WDDHEAKMLW
    LDSNYPLDKP ATSPGVARGE

421 CATTSGEPTD VESQVPNSSV TFSNIKFGPI GSTYSGTTGT
    PSSGSSSVIP PSSSVSTSSA

481 PSQTGTVAHW GQCGGIGYTG PTTCVAPYTC QVGNPYYSQC L
```

Features of SEQ ID NO: 12 (Amino Acid Positions):

| | |
|---|---|
| Signal Peptide | 1-18 |
| Cellobiohydrolase catalytic site (CBH 1) | 19-454 |

-continued

| | |
|---|---|
| Linker | 455-486 |
| Cellulose Binding Module (CBM 1) | 487-521 |

```
Signal Peptide Sequence of SEQ ID NO: 12:
MFPASALIALTFTAVAFG
```

DEFINITIONS

Cellobiohydrolase: The term "cellobiohydrolase" means a 1,4-beta-D-glucan cellobiohydrolase (E.C. 3.2.1.91) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teen et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters,* 149: 152-156; van Tilbeurgh and Claeyssens, 1985, *FEBS Letters,* 187: 283-288; and Tomme et al., 1988, *Eur. J. Biochem.* 170: 575-581. In the present invention, the Tomme et al. method can be used to determine cellobiohydrolase activity.

In one aspect, the polypeptides of the present invention have at least 20%, e.g., at least 40%, at least 50%, at least 60%, at least 70%, at least 80%, at least 90%, at least 95%, or at least 100% of the cellobiohydrolase activity of the mature polypeptide of SEQ ID NO: 2, SEQ ID NO: 4, SEQ ID NO: 6, SEQ ID NO: 8, SEQ ID NO: 10, or SEQ ID NO: 12.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 μmole of glucuronic or 4-O-methylglucuronic acid per minute at pH 5, 40° C.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 μmole of p-nitrophenolate anion produced per minute at 40° C., pH 5 from 1 mM p-nitrophenyl-beta-D-xyloside as substrate in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl(feruloyl) groups from esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Fragment: The term "fragment" means a polypeptide having one or more (e.g., several) amino acids absent from the amino and/or carboxyl terminus of a mature polypeptide; wherein the fragment has cellobiohydrolase activity. In one aspect, a fragment contains at least 20 amino acid residues, e.g., at least 30 to 464 amino acid residues or at least 50 to 460, 80 to 400, 100 to 350, 150 to 300, or 200 to 250, or any number in between, amino acid residues of SEQ ID NO: 2. In another aspect, a fragment contains at least 20 amino acid residues, e.g., at least 30 to 454 amino acid residues or at least 50 to 450, 80 to 400, 100 to 350, 150 to 300, or 200 to 250, or any number in between, amino acid residues of SEQ ID NO: 4. In another aspect, a fragment contains at least 20 amino acid residues, e.g., at least 30 to 452 amino acid residues or at least 50 to 440, 80 to 400, 100 to 350, 150 to 300, or 200 to 250, or any number in between, amino acid residues of SEQ ID NO: 6. In another aspect, a fragment contains at least 20 amino acid residues, e.g., at least 30 to 457 amino acid residues or at least 50 to 450, 80 to 400, 100 to 350, 150 to 300, or 200 to 250, or any number in between, amino acid residues of SEQ ID NO: 8. In another aspect, a fragment contains at least 20 amino acid residues, e.g., at least 30 to 518 amino acid residues or at least 50 to 500, 80 to 450, 100 to 350, 150 to 300, or 200 to 250, or any number in between, amino acid residues of SEQ ID NO: 10. In another aspect, a fragment contains at least 20 amino acid residues, e.g., at least 30 to 520 amino acid residues or at least 50 to 500, 80 to 450, 100 to 350, 150 to 300, or 200 to 250, or any number in between, amino acid residues of SEQ ID NO: 12.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y. Microbial hemicellulases. *Current Opinion In Microbiology,* 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 19 to 465 of SEQ ID NO: 2 based on the SignalP program (Nielsen et al., 1997, *Protein Engineering* 10: 1-6) that predicts amino acids 1 to 18 of SEQ ID NO: 2 are a signal peptide. In another aspect, the mature polypeptide is amino acids 1 to 465 of SEQ ID NO: 2. In another aspect, the mature polypeptide is amino acids 19 to 454 of SEQ ID NO: 4 based on the SignalP program that predicts amino acids 1 to 18 of SEQ ID NO: 4 are a signal peptide. In another aspect, the mature polypeptide is amino acids 1 to 454 of SEQ ID NO: 4. In another aspect, the mature polypeptide is amino acids 19 to 453 of SEQ ID NO: 6 based on the SignalP program that predicts amino acids 1 to 18 of SEQ ID NO: 6 are a signal peptide. In another aspect, the mature polypeptide is amino acids 1 to 453 of SEQ ID NO: 6. In another aspect, the mature polypeptide is amino acids 19 to 458 of SEQ ID NO: 8 based on the SignalP program that predicts amino acids 1 to 18 of SEQ ID NO: 8 are a signal peptide. In another aspect, the mature polypeptide is amino acids 1 to 458 of SEQ ID NO: 8. In another aspect, the mature polypeptide is amino acids 19 to 519 of SEQ ID NO: 10 based on the SignalP program that predicts amino acids 1 to 18 of SEQ ID NO: 10 are a signal peptide. In another aspect, the mature polypeptide is amino acids 1 to 519 of SEQ ID NO: 10. In another aspect, the mature polypeptide is amino acids 19 to 521 of SEQ ID NO: 12 based on the SignalP program that predicts amino acids 1 to 18 of SEQ ID NO: 12 are a signal peptide. In another aspect, the mature polypeptide is amino acids 1 to 521 of SEQ ID NO: 12. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having cellobiohydrolase activity. In one aspect, the mature polypeptide coding sequence is nucleotides 55 to 1499 of SEQ ID NO: 1 or the cDNA sequence thereof based on the SignalP program (Nielsen et al., 1997, supra) that predicts nucleotides 1 to 54 of SEQ ID NO: 1 encode a signal peptide. In another aspect, the mature polypeptide coding sequence is nucleotides 1 to 1499 of SEQ ID NO: 1 or the cDNA sequence thereof. In another aspect, the mature polypeptide coding sequence is nucleotides 55 to 1472 of SEQ ID NO: 3 or the cDNA sequence thereof based on the SignalP program that predicts nucleotides 1 to 54 of SEQ ID NO: 3 encode a signal peptide. In another aspect, the mature polypeptide coding sequence is nucleotides 1 to 1472 of SEQ ID NO: 3 or the cDNA sequence thereof. In another aspect, the mature polypeptide coding sequence is nucleotides 55 to 1489 of SEQ ID NO: 5 or the cDNA sequence thereof based on the SignalP program that predicts nucleotides 1 to 54 of SEQ ID NO: 5 encode a signal peptide. In another aspect, the mature polypeptide coding sequence is nucleotides 1 to 1489 of SEQ ID NO: 5 or the cDNA sequence thereof. In another aspect, the mature polypeptide coding sequence is nucleotides 55 to 1493 of SEQ ID NO: 7 or the cDNA sequence thereof based on the SignalP program that predicts nucleotides 1 to 54 of SEQ ID NO: 7 encode a signal peptide. In another aspect, the mature polypeptide coding sequence is nucleotides 1 to 1493 of SEQ ID NO: 7 or the cDNA sequence thereof. In another aspect, the mature polypeptide coding sequence is nucleotides 55 to 1789 of SEQ ID NO: 9 or the cDNA sequence thereof based on the SignalP program that predicts nucleotides 1 to 54 of SEQ ID NO: 9 encode a signal peptide. In another aspect, the mature polypeptide coding sequence is nucleotides 1 to 1789 of SEQ ID NO: 9 or the cDNA sequence thereof. In another aspect, the mature polypeptide coding sequence is nucleotides 55 to 1859 of SEQ ID NO: 11 or the cDNA sequence thereof based on the SignalP program that predicts nucleotides 1 to 54 of SEQ ID NO: 11 encode a signal peptide. In another aspect, the mature polypeptide coding sequence is nucleotides 1 to 1859 of SEQ ID NO: 11 or the cDNA sequence thereof.

Catalytic domain: The term "catalytic domain" means the portion of an enzyme containing the catalytic machinery of the enzyme.

Cellulose binding domain: The term "cellulose binding domain" means the portion of an enzyme that mediates binding of the enzyme to amorphous regions of a cellulose substrate. The cellulose binding domain (CBD) is found either at the N-terminal or at the C-terminal extremity of an enzyme. A CBD is also referred to as a cellulose binding module or CBM. In one embodiment the CBM is amino acids 483 to 519 of SEQ ID NO: 10. In one embodiment the CBM is amino acids 487 to 521 of SEQ ID NO: 12. The CBM is separated from the catalytic domain by a linker sequence. The linker is in one embodiment amino acids 455 to 482 of SEQ ID NO: 10. The linker is in one embodiment amino acids 455 to 486 of SEQ ID NO: 12.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In a preferred aspect, a mixture of CELLUCLAST® 1.5L (Novozymes NS, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Pretreated corn stover: The term "PCS" or "Pretreated Corn Stover" means a cellulosic material derived from corn stover by treatment with heat and dilute sulfuric acid, alkaline pretreatment, or neutral pretreatment.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the −nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the −nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having cellobiohydrolase activity. In one aspect, a subsequence contains at least 900 nucleotides, e.g., at least 1200 nucleotides or at least 1400 nucleotides of SEQ ID NO: 1, SEQ ID NO: 3, SEQ ID NO: 5, SEQ ID NO: 7, SEQ ID NO: 9, or SEQ ID NO: 11.

Variant: The term "variant" means a polypeptide having cellobiohydrolase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum commune, FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 whole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6 buffer.

DETAILED DESCRIPTION OF THE INVENTION

Polypeptides Having Cellobiohydrolase Activity

In an embodiment, the present invention relates to isolated polypeptides having a sequence identity to the mature polypeptide of SEQ ID NO: 2, of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have cellobiohydrolase activity. In an embodiment, the present invention relates to isolated polypeptides having a sequence identity to the mature polypeptide of SEQ ID NO: 4 of at least 78%, e.g., at least 79%, at least 80%, at least 85%, at least 90%, at least 91%, at least 92%, at least 93%, at least 94%, at least 95%, at least 96%, at least 97%, at least 98%, at least 99%, or 100%, which have cellobiohydrolase activity. In an embodiment, the present invention relates to isolated polypeptides having a sequence identity to the mature polypeptide of SEQ ID NO: 6 of at least 80%, e.g., at least 83%, at least 85%, at least 90%, at least 91%, at least 92%, at least 93%, at least 94%, at least 95%, at least 96%, at least 97%, at least 98%, at least 99%, or 100%, which have cellobiohydrolase activity. In an embodiment, the present invention relates to isolated polypeptides having a sequence identity to the mature polypeptide of SEQ ID NO: 8 of at least 82%, e.g., at least 83%, at least 85%, at least 90%, at least 91%, at least 92%, at least 93%, at least 94%, at least 95%, at least 96%, at least 97%, at least 98%, at least 99%, or 100%, which have cellobiohydrolase activity. In an embodiment, the present invention relates to isolated polypeptides having a sequence identity to the mature polypeptide of SEQ ID NO: 10 of at least 74%, e.g., at least 75%, at least 77%, at least 80%, at least 83%, at least 85%, at least 90%, at least 91%, at least 92%, at least 93%, at least 94%, at least 95%, at least 96%, at least 97%, at least 98%, at least 99%, or 100%, which have cellobiohydrolase activity. In an embodiment, the present invention relates to isolated polypeptides having a sequence identity to the mature polypeptide of SEQ ID NO: 12 of at least 75%, e.g., at least 77%, at least 80%, at least 83%, at least 85%, at least 90%, at least 91%, at least 92%, at least 93%, at least 94%, at least 95%, at least 96%, at least 97%, at least 98%, at least 99%, or 100%, which have cellobiohydrolase activity. In one aspect, the polypeptides differ by no more than 10 amino acids, e.g., 1, 2, 3, 4, 5, 6, 7, 8, or 9, from the mature polypeptide of SEQ ID NO: 2, SEQ ID NO: 4, SEQ ID NO: 6, SEQ ID NO: 8, SEQ ID NO: 10, or SEQ ID NO: 12.

A polypeptide of the present invention preferably comprises or consists of the amino acid sequence of SEQ ID NO: 2, SEQ ID NO: 4, SEQ ID NO: 6, SEQ ID NO: 8, SEQ ID NO: 10, or SEQ ID NO: 12, or an allelic variant thereof; or is a fragment thereof having cellobiohydrolase activity. In another aspect, the polypeptide comprises or consists of the mature polypeptide of SEQ ID NO: 2, SEQ ID NO: 4, SEQ ID NO: 6, SEQ ID NO: 8, SEQ ID NO: 10, or SEQ ID NO: 12. In another aspect, the polypeptide comprises or consists of amino acids 19 to 465 of SEQ ID NO: 2, amino acids 19 to 454 of SEQ ID NO: 4, amino acids 19 to 453 of SEQ ID NO: 6, amino acids 19 to 458 of SEQ ID NO: 8, amino acids 19 to 519 of SEQ ID NO: 10, or amino acids 19 to 521 of SEQ ID NO: 12.

In another embodiment, the present invention relates to an isolated polypeptide having cellobiohydrolase activity encoded by a polynucleotide that hybridizes under very low stringency conditions, or low stringency conditions, or medium stringency conditions, or medium-high stringency conditions, or high stringency conditions, or very high stringency conditions with (i) the mature polypeptide coding sequence of SEQ ID NO: 1, SEQ ID NO: 3, SEQ ID NO: 5, SEQ ID NO: 7, SEQ ID NO: 9, or SEQ ID NO: 11, (ii) the cDNA sequence thereof, or (iii) the full-length complement of (i) or (ii) (Sambrook et al., 1989, *Molecular Cloning, A Laboratory Manual,* 2d edition, Cold Spring Harbor, N.Y.).

The polynucleotide of SEQ ID NO: 1, SEQ ID NO: 3, SEQ ID NO: 5, SEQ ID NO: 7, SEQ ID NO: 9, or SEQ ID NO: 11, or a subsequence thereof, as well as the polypeptide of SEQ ID NO: 2, SEQ ID NO: 4, SEQ ID NO: 6, SEQ ID NO: 8, SEQ ID NO: 10, or SEQ ID NO: 12, or a fragment thereof, may be used to design nucleic acid probes to identify and clone DNA encoding polypeptides having cellobiohydrolase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having cellobiohydrolase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, SEQ ID NO: 3, SEQ ID NO: 5, SEQ ID NO: 7, SEQ ID NO: 9, or SEQ ID NO: 11 or a subsequence thereof, the carrier material is used in a Southern blot.

For purposes of the present invention, hybridization indicates that the polynucleotide hybridizes to a labeled nucleic acid probe corresponding to (i) SEQ ID NO: 1, SEQ ID NO: 3, SEQ ID NO: 5, SEQ ID NO: 7, SEQ ID NO: 9, or SEQ ID NO: 11; (ii) the mature polypeptide coding sequence of SEQ ID NO: 1, SEQ ID NO: 3, SEQ ID NO: 5, SEQ ID NO: 7, SEQ ID NO: 9, or SEQ ID NO: 11; (iii) the cDNA sequence thereof; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is a polynucleotide that encodes the polypeptide of SEQ ID NO: 2, SEQ ID NO: 4, SEQ ID NO: 6, SEQ ID NO: 8, SEQ ID NO: 10, or SEQ ID NO: 12; the mature polypeptide thereof; or a fragment thereof. In another aspect, the nucleic acid probe is SEQ ID NO: 1, SEQ ID NO: 3, SEQ ID NO: 5, SEQ ID NO: 7, SEQ ID NO: 9, or SEQ ID NO: 11; or the cDNA sequence thereof.

In another embodiment, the present invention relates to an isolated polypeptide having cellobiohydrolase activity encoded by a polynucleotide having a sequence identity to the mature polypeptide coding sequence of SEQ ID NO: 1, SEQ ID NO: 3, SEQ ID NO: 5, SEQ ID NO: 7, SEQ ID NO: 9, or SEQ ID NO: 11, or the cDNA sequence thereof, of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2, SEQ ID NO: 4, SEQ ID NO: 6, SEQ ID NO: 8, SEQ ID NO: 10, or SEQ ID NO: 12 comprising a substitution, deletion, and/or insertion at one or more (e.g., several) positions. In an embodiment, the number of amino acid substitutions, deletions and/or insertions introduced into the mature polypeptide of SEQ ID NO: 2, SEQ ID NO: 4, SEQ ID NO: 6, SEQ ID NO: 8, SEQ ID NO: 10, or SEQ ID NO: 12 is not more than 10, e.g., 1, 2, 3, 4, 5, 6, 7, 8 or 9. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for cellobiohydrolase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. *Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Cellobiohydrolase Activity

A polypeptide having cellobiohydrolase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a *Hohenbuehelia* polypeptide.

In another aspect, the polypeptide is a *Hohenbuehelia mastrucata* polypeptide, e.g., a polypeptide obtained from *Hohenbuehelia mastrucata* Strain NN009379.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Catalytic Domains

The present invention also relates to isolated polypeptides comprising a catalytic domain selected from the group consisting of:

(a) a catalytic domain having at least 60% sequence identity to the catalytic domain of SEQ ID NO: 2 (for example, amino acids 19 to 465 of SEQ ID NO: 2), SEQ ID NO: 4 (for example, amino acids 19 to 454 of SEQ ID NO: 4), SEQ ID NO: 6 (for example, amino acids 19 to 453 of SEQ ID NO: 6), SEQ ID NO: 8 (for example, amino acids 19 to 458 of SEQ ID NO: 8), SEQ ID NO: 10 (for example, amino acids 19 to 454 of SEQ ID NO: 10), or SEQ ID NO: 12 (for example, amino acids 19 to 454 of SEQ ID NO: 12);

(b) a catalytic domain encoded by a polynucleotide having at least 60% sequence identity to the catalytic domain coding sequence of SEQ ID NO: 1 (for example, nucleotides 55-211, 265-668, and 720-1499 of SEQ ID NO: 1), SEQ ID NO: 3 (for example, nucleotides 55-211, 264-664, and 723-1472 of SEQ ID NO: 3), SEQ ID NO: 5 (for example, nucleotides 55-211, 278-678, and 743-1489 of SEQ ID NO: 5), SEQ ID NO: 7 (for example, nucleotides 55-211, 269-672, and 735-1493 of SEQ ID NO: 7), SEQ ID NO: 9 (for example, nucleotides 55-190, 255-604, 658-729, and 787-1536 of SEQ ID NO: 9), or SEQ ID NO: 11 (for example, nucleotides 55-190, 246-586, 650-721, and 777-1535 of SEQ ID NO: 11);

(c) a variant of a catalytic domain comprising a substitution, deletion, and/or insertion of one or more (several) amino acids of the catalytic domain of SEQ ID NO: 2, SEQ ID NO: 4, SEQ ID NO: 6, SEQ ID NO: 8, SEQ ID NO: 10, or SEQ ID NO: 12; and (d) a fragment of a catalytic domain of (a), (b), or (c), which has cellobiohydrolase activity.

The catalytic domain preferably has a degree of sequence identity to the catalytic domain of SEQ ID NO: 2, SEQ ID NO: 4, SEQ ID NO: 6, SEQ ID NO: 8, SEQ ID NO: 10, or SEQ ID NO: 12 of at least 60%, e.g. at least 70%, at least 75%, at least 80%, at least 85%, at least 90%, at least 91%, at least 92%, at least 95%, at least 96%, at least 97%, at least 98%, at least 99%, or 100%. In an aspect, the catalytic domain comprises an amino acid sequence that differs by ten amino acids, e.g., by five amino acids, by four amino acids, by three amino acids, by two amino acids, and by one amino acid from the catalytic domain of SEQ ID NO: 2, SEQ ID NO: 4, SEQ ID NO: 6, SEQ ID NO: 8, SEQ ID NO: 10, or SEQ ID NO: 12.

The catalytic domain preferably comprises or consists of the catalytic domain of SEQ ID NO: 2 or an allelic variant thereof; or is a fragment thereof having cellobiohydrolase activity. In another preferred aspect, the catalytic domain comprises or consists of amino acids 19 to 465 of SEQ ID NO: 2.

The catalytic domain preferably comprises or consists of the catalytic domain of SEQ ID NO: 4 or an allelic variant thereof; or is a fragment thereof having cellobiohydrolase activity. In another preferred aspect, the catalytic domain comprises or consists of amino acids 19 to 454 of SEQ ID NO: 4.

The catalytic domain preferably comprises or consists of the catalytic domain of SEQ ID NO: 6 or an allelic variant thereof; or is a fragment thereof having cellobiohydrolase activity. In another preferred aspect, the catalytic domain comprises or consists of amino acids 19 to 453 of SEQ ID NO: 6.

The catalytic domain preferably comprises or consists of the catalytic domain of SEQ ID NO: 8 or an allelic variant thereof; or is a fragment thereof having cellobiohydrolase activity. In another preferred aspect, the catalytic domain comprises or consists of amino acids 19 to 458 of SEQ ID NO: 8.

The catalytic domain preferably comprises or consists of the catalytic domain of SEQ ID NO: 10 or an allelic variant thereof; or is a fragment thereof having cellobiohydrolase activity. In another preferred aspect, the catalytic domain comprises or consists of amino acids 19 to 454 of SEQ ID NO: 10.

The catalytic domain preferably comprises or consists of the catalytic domain of SEQ ID NO: 12 or an allelic variant thereof; or is a fragment thereof having cellobiohydrolase activity. In another preferred aspect, the catalytic domain comprises or consists of amino acids 19 to 454 of SEQ ID NO: 12.

In an embodiment, the catalytic domain may be encoded by a polynucleotide that hybridizes under very low stringency conditions, or low stringency conditions, or medium stringency conditions, or medium-high stringency conditions, or high stringency conditions, or very high stringency conditions (as defined above) with (i) the catalytic domain coding sequence of SEQ ID NO: 1, SEQ ID NO: 3, SEQ ID NO: 5, SEQ ID NO: 7, SEQ ID NO: 9, or SEQ ID NO: 11, (ii) the cDNA sequence contained in the catalytic domain coding sequence of SEQ ID NO: 1, SEQ ID NO: 3, SEQ ID NO: 5, SEQ ID NO: 7, SEQ ID NO: 9, or SEQ ID NO: 11, or (iii) the full-length complementary strand of (i) or (ii) (J. Sambrook et al., 1989, supra).

The catalytic domain may be encoded by a polynucleotide having a degree of sequence identity to the catalytic domain coding sequence of SEQ ID NO: 1, SEQ ID NO: 3, SEQ ID NO: 5, SEQ ID NO: 7, SEQ ID NO: 9, or SEQ ID NO: 11 of at least 60%, e.g. at least 70%, at least 75%, at least 80%, at least 85%, at least 90%, at least 91%, at least 92%, at least 95%, at least 96%, at least 97%, at least 98%, at least 99%, or 100%, which encode a polypeptide having cellobiohydrolase activity.

In one aspect, the polynucleotide encoding the catalytic domain comprises or consists of nucleotides 55-211, 265-668, and 720-1499 of SEQ ID NO: 1 or the cDNA sequence thereof.

In one aspect, the polynucleotide encoding the catalytic domain comprises or consists of nucleotides 55-211, 264-664, and 723-1472 of SEQ ID NO: 3 or the cDNA sequence thereof.

In one aspect, the polynucleotide encoding the catalytic domain comprises or consists of nucleotides 55-211, 278-678, and 743-1489 of SEQ ID NO: 5 or the cDNA sequence thereof.

In one aspect, the polynucleotide encoding the catalytic domain comprises or consists of nucleotides 55-211, 269-672, and 735-1493 of SEQ ID NO: 7 or the cDNA sequence thereof.

In one aspect, the polynucleotide encoding the catalytic domain comprises or consists of nucleotides 55-190, 255-604, 658-729, and 787-1536 of SEQ ID NO: 9 or the cDNA sequence thereof.

In one aspect, the polynucleotide encoding the catalytic domain comprises or consists of nucleotides 55-190, 246-586, 650-721, and 777-1535 of SEQ ID NO: 11 or the cDNA sequence thereof.

Polynucleotides

The present invention also relates to isolated polynucleotides encoding a polypeptide of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Hohenbuehelia*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, SEQ ID NO: 3, SEQ ID NO: 5, SEQ ID NO: 7, SEQ ID NO: 9, or SEQ ID NO: 11, or the cDNA sequence thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dada (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae enolase* (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae enolase, Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae enolase* (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma.*

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (*Praha*) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, Bio/Technology 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and (b) recovering the polypeptide. In a preferred aspect, the cell is a *Hohenbuehelia* cell. In a more preferred aspect, the cell is a *Hohenbuehelia mastrucata* cell. In a most preferred aspect, the cell is *Hohenbuehelia mastrucata* Strain NN009379.

The present invention also relates to methods of producing a polypeptide of the present invention, comprising (a) cultivating a recombinant host cell of the present invention under conditions conducive for production of the polypeptide; and (b) recovering the polypeptide.

The host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana.*

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The expression construct is conveniently a nucleic acid construct that comprises a polynucleotide encoding a polypeptide or domain operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide or domain is desired to be expressed. For instance, the expression of the gene encoding a polypeptide or domain may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide or domain can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Compositions

The present invention also relates to compositions comprising a polypeptide of the present invention. Preferably, the compositions are enriched in such a polypeptide. The term "enriched" indicates that the cellobiohydrolase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as one or more (e.g., several) enzymes selected from the group consisting of a cellulase, a hemicellulase, GH61 polypeptide, an expansin, an esterase, a laccase, a ligninolytic enzyme, a pectinase, a peroxidase, a protease, and a swollenin.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to the following processes for using the polypeptides having cellobiohydrolase activity, or compositions thereof.

The present invention also relates to processes for degrading a cellulosic material, comprising: treating the cellulosic material with an enzyme composition in the presence of a polypeptide having cellobiohydrolase activity of the present invention. In one aspect, the processes further comprise recovering the degraded or converted cellulosic material. Soluble products of degradation or conversion of the cellulosic material can be separated from insoluble cellulosic material using a method known in the art such as, for example, centrifugation, filtration, or gravity settling.

The present invention also relates to processes of producing a fermentation product, comprising: (a) saccharifying a cellulosic material with an enzyme composition in the presence of a polypeptide having cellobiohydrolase activity of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a polypeptide having cellobiohydrolase activity of the present invention. In one aspect, the fermenting of the cellulosic material produces a fermentation product. In another aspect, the processes further comprise recovering the fermentation product from the fermentation.

The processes of the present invention can be used to saccharify the cellulosic material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic material typically involves pretreatment, enzymatic hydrolysis (saccharification), and fermentation.

The processing of the cellulosic material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.*

25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include fluidized bed, upflow blanket, immobilized, and extruder type reactors for hydrolysis and/or fermentation.

Pretreatment.

In practicing the processes of the present invention, any pretreatment process known in the art can be used to disrupt plant cell wall components of the cellulosic material (Chandra et al., 2007, Substrate pretreatment: The key to effective enzymatic hydrolysis of lignocellulosics?, *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, *Pretreatment of lignocellulosic wastes to improve ethanol and biogas production: A review, Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on temperature range and addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze explosion (AFEX).

Lime pretreatment is performed with calcium oxide or calcium hydroxide at temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. and Biotechnol. Vol.* 105-108, p. 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt % acid, e.g., 0.05 to 5 wt % acid or 0.1 to 2 wt % acid. The acid is contacted with the cellulosic material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material is present during pretreatment in amounts preferably between 10-80 wt %, e.g., 20-70 wt % or 30-60 wt %, such as around 40 wt %. The pretreated cellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification.

In the hydrolysis step, also known as saccharification, the cellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition in the presence of a polypeptide having cellobiohydrolase activity of the present invention. The enzymes of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme(s), i.e., optimal for the enzyme(s). The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5.0 to about 5.5. The dry solids content is in the range of preferably about 5 to about 50 wt %, e.g., about 10 to about 40 wt % or about 20 to about 30 wt %.

The enzyme compositions can comprise any protein useful in degrading the cellulosic material.

In one aspect, the enzyme composition comprises or further comprises one or more (e.g., several) proteins selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a polypeptide having cellulolytic enhancing activity. In another aspect, the enzyme composition comprises a cellobiohydrolase and a polypeptide having cellulolytic enhancing activity. In another aspect, the enzyme composition comprises a beta-glucosidase and a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a polypeptide having cellulolytic enhancing activity. In another aspect, the enzyme composition comprises an endoglucanase, a beta-glucosidase, and a polypeptide having cellulolytic enhancing activity. In another aspect, the enzyme composition comprises a cellobiohydrolase, a beta-glucosidase, and a polypeptide having cellulolytic enhancing activity. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin.

In the processes of the present invention, the enzyme(s) can be added prior to or during fermentation, e.g., during saccharification or during or after propagation of the fermenting microorganism(s).

One or more (e.g., several) components of the enzyme composition may be wild-type proteins, recombinant proteins, or a combination of wild-type proteins and recombinant proteins. For example, one or more (e.g., several) components may be native proteins of a cell, which is used as a host cell to express recombinantly one or more (e.g., several) other components of the enzyme composition. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a crude fermentation broth with or without cells removed, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and polypeptides having cellobiohydrolase activity depend on several factors including, but not limited to, the mixture of component cellulolytic enzymes, the cellulosic material, the concentration of cellulosic material, the pretreatment(s) of the cellulosic material, temperature, time, pH, and inclusion of fermenting organism (e.g., yeast for Simultaneous Saccharification and Fermentation).

In one aspect, an effective amount of cellulolytic or hemicellulolytic enzyme to the cellulosic material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material.

In another aspect, an effective amount of a polypeptide having cellobiohydrolase activity to the cellulosic material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic material.

In another aspect, an effective amount of a polypeptide having cellobiohydrolase activity to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic material, e.g., GH61 polypeptides having cellulolytic enhancing activity (collectively hereinafter "polypeptides having enzyme activity") can be derived or obtained from any suitable origin, including, bacterial, fungal, yeast, plant, or mammalian origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus, Caldicellulosiruptor, Acidothermus, Thermobifidia*, or *Oceanobacillus* polypeptide having enzyme activity, or a Gram negative bacterial polypeptide such as an *E. coli, Pseudomonas, Salmonella, Campylobacter, Helicobacter, Flavobacterium, Fusobacterium, Ilyobacter, Neisseria*, or *Ureaplasma* polypeptide having enzyme activity.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide having enzyme activity.

In another aspect, the polypeptide is a *Streptococcus equisimilis, Streptococcus pyogenes, Streptococcus uberis*, or *Streptococcus equi* subsp. *Zooepidemicus* polypeptide having enzyme activity.

In another aspect, the polypeptide is a *Streptomyces achromogenes, Streptomyces avermitilis, Streptomyces coelicolor, Streptomyces griseus*, or *Streptomyces lividans* polypeptide having enzyme activity.

The polypeptide having enzyme activity may also be a fungal polypeptide, and more preferably a yeast polypeptide such as a *Candida, Kluyveromyces, Pichia, Saccharomyces, Schizosaccharomyces*, or *Yarrowia* polypeptide having enzyme activity; or more preferably a filamentous fungal polypeptide such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide having enzyme activity.

In one aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having enzyme activity.

In another aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride*, or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC™ CTec (Novozymes NS), CELLIC™ CTec2 (Novozymes NS), CELLUCLAST™ (Novozymes NS), NOVOZYM™ 188 (Novozymes NS), CELLUZYME™ (Novozymes NS), CEREFLO™ (Novozymes NS), and ULTRAFLO™ (Novozymes NS), ACCELERASE™ (Genencor Int.), LAMINEX™ (Genencor Int.), SPEZYME™ CP (Genencor Int.), FILTRASE® NL (DSM); METHAPLUS® S/L 100 (DSM). ROHAMENT™ 7069 W (Röhm GmbH), FIBREZYME® LDI (Dyadic International, Inc.), FIBREZYME® LBR (Dyadic International, Inc.), or VISCOSTAR® 150L (Dyadic International, Inc.). The cellulase enzymes are added in amounts effective from about 0.001 to about 5.0 wt % of solids, e.g., about 0.025 to about 4.0 wt % of solids or about 0.005 to about 2.0 wt % of solids.

Examples of bacterial endoglucanases that can be used in the processes of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention, include, but are not limited to, a *Trichoderma reesei* endoglucanase I (Penttila et al., 1986, *Gene* 45: 253-263, *Trichoderma reesei* Cel7B endoglucanase I (GENBANK™ accession no. M15665), *Trichoderma reesei* endoglucanase II (Saloheimo, et al., 1988, *Gene* 63:11-22), *Trichoderma reesei* Cel5A endoglucanase II (GENBANK™ accession no. M19373), *Trichoderma reesei* endoglucanase III (Okada et al., 1988, *Appl. Environ. Microbiol.* 64: 555-563, GENBANK™ accession no. AB003694), *Trichoderma reesei* endoglucanase V (Saloheimo et al., 1994, *Molecular Microbiology* 13: 219-228, GENBANK™ accession no. Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Erwinia carotovara* endoglucanase (Saarilahti et al., 1990, *Gene* 90: 9-14), *Fusarium oxysporum* endoglucanase (GENBANK™ accession no. L29381), *Humicola grisea* var. *thermoidea* endoglucanase (GENBANK™ accession no. AB003107), *Melanocarpus albomyces* endoglucanase (GENBANK™ accession no. MAL515703), *Neurospora crassa* endoglucanase (GENBANK™ accession no. XM_324477), *Humicola insolens* endoglucanase V, *Myceliophthora thermophila* CBS 117.65 endoglucanase, basidiomycete CBS 495.95 endoglucanase, basidiomycete CBS 494.95 endoglucanase, *Thielavia terrestris* NRRL 8126 CEL6B endoglucanase, *Thielavia terrestris* NRRL 8126 CEL6C endoglucanase, *Thielavia terrestris NRRL* 8126 CEL7C endoglucanase, *Thielavia terrestris* NRRL 8126 CEL7E endoglucanase, *Thielavia terrestris* NRRL 8126 CEL7F endoglucanase, *Cladorrhinum foecundissimum* ATCC 62373 CEL7A endoglucanase, and *Trichoderma reesei* strain No. VTT-D-80133 endoglucanase (GENBANK™ accession no. M15665).

Examples of cellobiohydrolases useful in the present invention include, but are not limited to, *Aspergillus aculeatus* cellobiohydrolase II (WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Thielavia* hyrcanie cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydralase II (WO 2010/057086).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 2002/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637.

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 5,457,046, U.S. Pat. No. 5,648,263, and U.S. Pat. No. 5,686,593.

In the processes of the present invention, any GH61 polypeptide having cellulolytic enhancing activity can be used.

Examples of GH61 polypeptides having cellulolytic enhancing activity useful in the processes of the present invention include, but are not limited to, GH61 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290), *Myceliophthora thermophila* (WO 2009/085935, WO 2009/085859, WO 2009/085864, WO 2009/085868), *Aspergillus fumigatus* (WO 2010/138754), GH61 polypeptides from *Penicillium pinophilum* (WO 2011/005867), *Thermoascus* sp. (WO 2011/039319), *Penicillium* sp. (WO 2011/041397), and *Thermoascus crustaceous* (WO 2011/041504).

In one aspect, the GH61 polypeptide having cellulolytic enhancing activity is used in the presence of a soluble activating divalent metal cation according to WO 2008/151043, e.g., manganese sulfate.

In one aspect, the GH61 polypeptide having cellulolytic enhancing activity is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1,2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of thebicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothieno-pyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl)furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of the nitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound described above is about 0.1 μM to about 1 M, e.g., about 0.5 μM to about 0.75 M, about 0.75 μM to about 0.5 M, about 1 μM to about 0.25 M, about 1 μM to about 0.1 M, about 5 μM to about 50 mM, about 10 μM to about 25 mM, about 50 μM to about 25 mM, about 10 μM to about 10 mM, about 5 μM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5, about $10^{-6}$ to about 2.5 g, about $10^{-6}$ to about 1 g, about $10^{-6}$ to about 1 g, about $10^{-6}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes NS), CELLIC™ HTec (Novozymes NS), CELLIC™ HTec2 (Novozymes NS), VISCOZYME® (Novozymes NS), ULTRAFLO® (Novozymes NS), PULPZYME® HC (Novozymes NS), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thielavia terrestris* NRRL 8126 (WO 2009/079210), and *Trichophaea saccata* GH10 (WO 2011/057083).

Examples of beta-xylosidases useful in the processes of the present invention include, but are not limited to, beta-xylosidases from *Neurospora crassa* (SwissProt accession number Q7SOW4), *Trichoderma reesei* (UniProtKB/TrEMBL accession number Q92458), and *Talaromyces emersonii* (SwissProt accession number Q8X212).

Examples of acetylxylan esterases useful in the processes of the present invention include, but are not limited to, acetylxylan esterases from *Aspergillus aculeatus* (WO 2010/108918), *Chaetomium globosum* (Uniprot accession number Q2GWX4), *Chaetomium gracile* (GeneSeqP accession number AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt accession number q7s259), *Phaeosphaeria nodorum* (Uniprot accession number QOUHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt Accession number A1D9T4), *Neurospora crassa* (UniProt accession number Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP accession number AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt accession number alcc12), *Aspergillus fumigatus* (SwissProt accession number Q4WW45), *Aspergillus niger* (Uniprot accession number Q96WX9), *Aspergillus terreus* (SwissProt accession number QOCJP9), *Humicola insolens* (WO 2010/014706), *Penicillium aurantiogriseum* (WO 2009/068565), *Talaromyces emersonii* (UniProt accession number Q8X211), and *Trichoderma reesei* (Uniprot accession number Q99024).

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Preferred yeast includes strains of *Candida, Kluyveromyces*, and *Saccharomyces*, e.g., *Candida sonorensis, Kluyveromyces marxianus*, and *Saccharomyces cerevisiae.*

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*.

Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans; Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis,* and *C. scehatae; Clostridium*, such as *C. acetobutylicum, C. thermocellum*, and *C. phytofermentans; E. coli*, especially *E. coli* strains that have been genetically modified to improve the yield of ethanol; *Geobacillus* sp.; *Hansenula*, such as *Hansenula anomala; Klebsiella*, such as *K. oxytoca; Kluyveromyces*, such as *K. marxianus, K. lactis, K. thermotolerans*, and *K. fragilis; Schizosaccharomyces*, such as *S. pombe; Thermoanaerobacter*, such as *Thermoanaerobacter saccharolyticum*; and *Zymomonas*, such as *Zymomonas mobllis.*

In a preferred aspect, the yeast is a *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida blankii*. In another more preferred aspect, the yeast is *Candida brassicae*. In another more preferred aspect, the yeast is *Candida diddensii*. In another more preferred aspect, the yeast is *Candida entomophiliia*. In another more preferred aspect, the yeast is *Candida pseudotropicalis*. In another more preferred aspect, the yeast is *Candida scehatae*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum.*

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium phytofermentans*. In another more preferred aspect, the bacterium is *Clostridium thermocellum*. In another more preferred aspect, the bacterium is *Geobacillus* sp. In another more preferred aspect, the bacterium is a *Thermoanaerobacter*. In another more preferred aspect, the bacterium is *Thermoanaerobacter saccharolyticum*. In another preferred aspect, the bacterium is a *Zymomonas*. In another more preferred aspect, the bacterium is *Zymomonas mobilis.*

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (cofermentation) (Chen and Ho, 1993, Cloning and improving the expression of *Pichia stipitis* xylose reductase gene in *Saccharomyces cerevisiae, Appl. Biochem. Biotechnol.* 39-40: 135-147; Ho et al., 1998, *Genetically engineered Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae, Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli, Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis, Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis.*

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2\times10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the processes of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, *Production of acetone*, butanol and ethanol by *Clostridium beijerinckii* BA101 and in situ recovery by gas stripping, *World Journal of Microbiology and Biotechnology* 19 (6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

In another preferred aspect, the fermentation product is isoprene.

In another preferred aspect, the fermentation product is a ketone. It will be understood that the term "ketone" encompasses a substance that contains one or more ketone moieties.

In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol.% can be obtained, which can be used as, for example, fuel ethanol, drinking ethanol, i.e., potable neutral spirits, or industrial ethanol.

Signal Peptide

The present invention also relates to an isolated polynucleotide encoding a signal peptide comprising or consisting of amino acids 1 to 18 of SEQ ID NO: 2, amino acids 1 to 18 of SEQ ID NO: 4, amino acids 1 to 18 of SEQ ID NO: 6, amino acids 1 to 18 of SEQ ID NO: 8, amino acids 1 to 18 of SEQ ID NO: 10, or amino acids 1 to 18 of SEQ ID NO: 12. The polynucleotide may further comprise a gene encoding a protein, which is operably linked to the signal peptide. The protein is preferably foreign to the signal peptide. In one aspect, the polynucleotide encoding the signal peptide is nucleotides 1 to 54 of SEQ ID NO: 1. In another aspect, the polynucleotide encoding the signal peptide is nucleotides 1 to 54 of SEQ ID NO: 3. In another aspect, the polynucleotide encoding the signal peptide is nucleotides 1 to 54 of SEQ ID NO: 5. In another aspect, the polynucleotide encoding the signal peptide is nucleotides 1 to 54 of SEQ ID NO: 7. In another aspect, the polynucleotide encoding the signal peptide is nucleotides 1 to 54 of SEQ ID NO: 9. In another aspect, the polynucleotide encoding the signal peptide is nucleotides 1 to 54 of SEQ ID NO: 11.

The present invention also relates to nucleic acid constructs, expression vectors and recombinant host cells comprising such polynucleotides.

The present invention also relates to methods of producing a protein, comprising (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

The gene may be obtained from any prokaryotic, eukaryotic, or other source.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A nucleic acid construct comprising a polynucleotide encoding a polypeptide, wherein the polynucleotide is operably linked to one or more heterologous control sequences that direct production of the polypeptide in an expression host, and wherein the polypeptide:

(a) has at least 95% sequence identity to the sequence of amino acids 19-465 of SEQ ID NO: 2, or (b) is a fragment of the sequence of amino acids 19-465 of SEQ ID NO: 2, wherein the polypeptide has cellobiohydrolase activity.

2. The nucleic acid construct of claim 1, wherein the polypeptide having cellobiohydrolase activity has at least 97% sequence identity to the sequence of amino acids 19-465 of SEQ ID NO: 2.

3. The nucleic acid construct of claim 1, wherein the polypeptide having cellobiohydrolase activity is a variant of the sequence of amino acids 19-465 of SEQ ID NO: 2, comprising a substitution, deletion, and/or insertion of one or more amino acids, wherein the variant has at least 98% sequence identity to the sequence of amino acids 19-465 of SEQ ID NO: 2.

4. The nucleic acid construct of claim 1, wherein the polypeptide having cellobiohydrolase activity comprises the sequence of amino acids 19-465 of SEQ ID NO: 2.

5. The nucleic acid construct of claim 1, wherein the polypeptide having cellobiohydrolase activity is a fragment of the sequence of amino acids 19-465 of SEQ ID NO: 2.

6. The nucleic acid construct of claim 2, wherein the polypeptide having cellobiohydrolase activity further comprises a cellulose binding domain.

7. The nucleic acid construct of claim 3, wherein the polypeptide having cellobiohydrolase activity further comprises a cellulose binding domain.

8. The nucleic acid construct of claim 4, wherein the polypeptide having cellobiohydrolase activity further comprises a cellulose binding domain.

9. The nucleic acid construct of claim 5, wherein the polypeptide having cellobiohydrolase activity further comprises a cellulose binding domain.

10. A process for degrading a cellulosic material, comprising treating the cellulosic material with a polypeptide having cellobiohydrolase activity, an endoglucanase, a beta-glucosidase, and a GH61 polypeptide having cellulolytic enhancing activity, wherein the polypeptide having cellobiohydrolase activity:

(a) has at least 95% sequence identity to the sequence of amino acids 19-465 of SEQ ID NO: 2, or (b) is a fragment of the sequence of amino acids 19-465 of SEQ ID NO: 2.

11. A process for producing a fermentation product, comprising:

(a) saccharifying a cellulosic material with an enzyme composition in the presence of a polypeptide having cellobiohydrolase activity, an endoglucanase, a beta-glucosidase, and a GH61 polypeptide having cellulolytic enhancing activity; and (b) fermenting the saccharified cellulosic material with one or more fermenting microorganisms to produce the fermentation product, wherein the polypeptide having cellobiohydrolase activity:

(i) has at least 95% sequence identity to the sequence of amino acids 19-465 of SEQ ID NO: 2, or (ii) is a fragment of the sequence of amino acids 19-465 of SEQ ID NO: 2.

12. The process of claim 11, further comprising recovering the fermentation product.

13. The process of claim 11, wherein the polypeptide having cellobiohydrolase activity has at least 97% sequence identity to the sequence of amino acids 19-465 of SEQ ID NO: 2.

14. The process of claim 13, wherein the polypeptide having cellobiohydrolase activity further comprises a cellulose binding domain.

15. The process of claim 14, further comprising recovering the fermentation product.

16. The nucleic acid construct of claim 1, wherein the polypeptide having cellobiohydrolase activity has at least 95% sequence identity to the sequence of amino acids 19-465 of SEQ ID NO: 2.

17. The nucleic acid construct of claim 16 wherein the polypeptide having cellobiohydrolase activity further comprises a cellulose binding domain.

18. A recombinant host cell comprising the nucleic acid construct of claim 1.

19. The process of claim 10, wherein the polypeptide having cellobiohydrolase activity has at least 97% sequence identity to the sequence of amino acids 19-465 of SEQ ID NO: 2.

20. The process of claim 19, wherein the polypeptide having cellobiohydrolase activity further comprises a cellulose binding domain.

* * * * *

SEQUENCE LISTING

```
<160> NUMBER OF SEQ ID NOS: 12

<210> SEQ ID NO 1
<211> LENGTH: 1502
<212> TYPE: DNA
<213> ORGANISM: Hohenbuehelia mastrucata
<220> FEATURE:
<221> NAME/KEY: CDS
<222> LOCATION: (1)..(211)
<220> FEATURE:
<221> NAME/KEY: sig_peptide
```

```
<222> LOCATION: (1)..(54)
<220> FEATURE:
<221> NAME/KEY: mat_peptide
<222> LOCATION: (55)..()
<220> FEATURE:
<221> NAME/KEY: Intron
<222> LOCATION: (212)..(264)
<220> FEATURE:
<221> NAME/KEY: CDS
<222> LOCATION: (265)..(668)
<220> FEATURE:
<221> NAME/KEY: Intron
<222> LOCATION: (669)..(719)
<220> FEATURE:
<221> NAME/KEY: CDS
<222> LOCATION: (720)..(1499)

<400> SEQUENCE: 1

atg ttt cgc agt att acc ctt gta ccg ctc gtc ttc ttt gct atc gtc       48
Met Phe Arg Ser Ile Thr Leu Val Pro Leu Val Phe Phe Ala Ile Val
            -15                 -10                 -5

tac ggc cag caa cca tcc gtg atc act ccc gaa tac cat cct ccc cta       96
Tyr Gly Gln Gln Pro Ser Val Ile Thr Pro Glu Tyr His Pro Pro Leu
    -1  1               5                   10

aca atc tac aaa tgc act tca agc ggt ggc tgc cag tca caa acc cgt      144
Thr Ile Tyr Lys Cys Thr Ser Ser Gly Gly Cys Gln Ser Gln Thr Arg
15                  20                  25                  30

tcc gtc gtt ctt gac gcg agc tgg cgc tgg gcg tac gag aaa acg tcc      192
Ser Val Val Leu Asp Ala Ser Trp Arg Trp Ala Tyr Glu Lys Thr Ser
                35                  40                  45

cac gac atc tgt atc tca g gttcggttgc attcgtgcat tgcatagtgt           241
His Asp Ile Cys Ile Ser
            50

ttaatctcat taagtcgtgg aag ac  ggc aac tgg aac acc ctc gtc tgc att    293
                          Asp Gly Asn Trp Asn Thr Leu Val Cys Ile
                                  55                  60

aac ccc gtt atc tgc gcg cag gtt tgc gcc ctt gat ggc gtt gac tat      341
Asn Pro Val Ile Cys Ala Gln Val Cys Ala Leu Asp Gly Val Asp Tyr
        65                  70                  75

tct gcg acg tac ggc atc acg acg agc ggc agc act ctc acc ctc cga      389
Ser Ala Thr Tyr Gly Ile Thr Thr Ser Gly Ser Thr Leu Thr Leu Arg
    80                  85                  90

tat gtc aca caa agt ggg aga ggc acg aat gtc ggc tct cgc gtg ttt      437
Tyr Val Thr Gln Ser Gly Arg Gly Thr Asn Val Gly Ser Arg Val Phe
95                  100                 105                 110

ctg ctg gaa aac gag aac gaa tac cag gca ttc aat ctc aag aat caa      485
Leu Leu Glu Asn Glu Asn Glu Tyr Gln Ala Phe Asn Leu Lys Asn Gln
                115                 120                 125

gaa ttc gcc ttc gat gtt gat aca tcg cag ctc ccg tgc ggc ctc aag      533
Glu Phe Ala Phe Asp Val Asp Thr Ser Gln Leu Pro Cys Gly Leu Lys
            130                 135                 140

ggc tcg ctc tac ttc acg gag atg gac aca gat ggg ggc ttg gcc aag      581
Gly Ser Leu Tyr Phe Thr Glu Met Asp Thr Asp Gly Gly Leu Ala Lys
        145                 150                 155

ttc ccg gac aac gat gca ggg gcg aaa ttt ggc aca ggc tat tgc gac      629
Phe Pro Asp Asn Asp Ala Gly Ala Lys Phe Gly Thr Gly Tyr Cys Asp
    160                 165                 170

gct cag tgc ccg cat gaa gtt aag tgg cag aac ggc gag gtacgtcttt       678
Ala Gln Cys Pro His Glu Val Lys Trp Gln Asn Gly Glu
175                 180                 185

gagatcgaac acaaaacatc gagtttacaa tcctacggca g gct aac atg ttg gac    734
                                              Ala Asn Met Leu Asp
                                                      190
```

```
tgg ttc ccg att tcg aat gat gag agg gcc tgg aga ggc aag tac ggc      782
Trp Phe Pro Ile Ser Asn Asp Glu Arg Ala Trp Arg Gly Lys Tyr Gly
        195                 200                 205

gcc tgc tgt acc caa att gat ctg tgg gaa gcg aac caa tat tct gcg      830
Ala Cys Cys Thr Gln Ile Asp Leu Trp Glu Ala Asn Gln Tyr Ser Ala
    210                 215                 220

gct ttc acc ccg cac cct tgc gtt gag aag gtc cgc tgc gaa aat gta      878
Ala Phe Thr Pro His Pro Cys Val Glu Lys Val Arg Cys Glu Asn Val
225                 230                 235                 240

gtc gac tgc ggg gat tgg agc aac aga tac gat ggc tac tgc gat aaa      926
Val Asp Cys Gly Asp Trp Ser Asn Arg Tyr Asp Gly Tyr Cys Asp Lys
                245                 250                 255

gat ggc tgt gac tac aac cct tac cgc ctc ggt gac ccg agc ttc ctc      974
Asp Gly Cys Asp Tyr Asn Pro Tyr Arg Leu Gly Asp Pro Ser Phe Leu
            260                 265                 270

ggt cca ggc aag gct gta gac acg acg caa aag att acc gtc atc acg     1022
Gly Pro Gly Lys Ala Val Asp Thr Thr Gln Lys Ile Thr Val Ile Thr
        275                 280                 285

caa ttc atc act gac gac aac acc cca aat ggc aat ctc gtg gag att     1070
Gln Phe Ile Thr Asp Asp Asn Thr Pro Asn Gly Asn Leu Val Glu Ile
    290                 295                 300

cgg cgc atc ttt agg caa aac ggg atc atc att cag aac gcc cgg gtc     1118
Arg Arg Ile Phe Arg Gln Asn Gly Ile Ile Ile Gln Asn Ala Arg Val
305                 310                 315                 320

aac gtt ccc ggc atc cca ccg tac gac tcg atc aca gac gac ttc tgc     1166
Asn Val Pro Gly Ile Pro Pro Tyr Asp Ser Ile Thr Asp Asp Phe Cys
                325                 330                 335

agc acg cag aag acg gcg ttc aac gac cag aac tac ttt gcg tcg ctg     1214
Ser Thr Gln Lys Thr Ala Phe Asn Asp Gln Asn Tyr Phe Ala Ser Leu
            340                 345                 350

ggt gga ctt ggg cag gtg ggg cat ggg atg gat aat ggc ttg gta cta     1262
Gly Gly Leu Gly Gln Val Gly His Gly Met Asp Asn Gly Leu Val Leu
        355                 360                 365

gcg atg agt ctc ctg gat gat cct gat cgc caa ttg ctt tgg ctc gac     1310
Ala Met Ser Leu Leu Asp Asp Pro Asp Arg Gln Leu Leu Trp Leu Asp
    370                 375                 380

agc aca tat ccc ccg gat agg gat gct gct gag cca ggc gtt acg cga     1358
Ser Thr Tyr Pro Pro Asp Arg Asp Ala Ala Glu Pro Gly Val Thr Arg
385                 390                 395                 400

gga act tgc gcg acg gct tcg ggt aag cct gtt gat ctt gag gct gaa     1406
Gly Thr Cys Ala Thr Ala Ser Gly Lys Pro Val Asp Leu Glu Ala Glu
                405                 410                 415

tcg ccc aat gcc tcg gtc atg ttc tcc aac atc cgg tac ggg gac att     1454
Ser Pro Asn Ala Ser Val Met Phe Ser Asn Ile Arg Tyr Gly Asp Ile
            420                 425                 430

gga tca acg tac cca atg cct ggc tcc gga tcg act tgt gca tgt taa     1502
Gly Ser Thr Tyr Pro Met Pro Gly Ser Gly Ser Thr Cys Ala Cys
        435                 440                 445


<210> SEQ ID NO 2
<211> LENGTH: 465
<212> TYPE: PRT
<213> ORGANISM: Hohenbuehelia mastrucata

<400> SEQUENCE: 2

Met Phe Arg Ser Ile Thr Leu Val Pro Leu Val Phe Phe Ala Ile Val
            -15                 -10                 -5

Tyr Gly Gln Gln Pro Ser Val Ile Thr Pro Glu Tyr His Pro Pro Leu
    -1  1               5                   10

Thr Ile Tyr Lys Cys Thr Ser Ser Gly Gly Cys Gln Ser Gln Thr Arg
```

```
15                  20                  25                  30

Ser Val Val Leu Asp Ala Ser Trp Arg Trp Ala Tyr Glu Lys Thr Ser
                35                  40                  45

His Asp Ile Cys Ile Ser Asp Gly Asn Trp Asn Thr Leu Val Cys Ile
            50                  55                  60

Asn Pro Val Ile Cys Ala Gln Val Cys Ala Leu Asp Gly Val Asp Tyr
        65                  70                  75

Ser Ala Thr Tyr Gly Ile Thr Thr Ser Gly Ser Thr Leu Thr Leu Arg
    80                  85                  90

Tyr Val Thr Gln Ser Gly Arg Gly Thr Asn Val Gly Ser Arg Val Phe
95                  100                 105                 110

Leu Leu Glu Asn Glu Asn Glu Tyr Gln Ala Phe Asn Leu Lys Asn Gln
                115                 120                 125

Glu Phe Ala Phe Asp Val Asp Thr Ser Gln Leu Pro Cys Gly Leu Lys
            130                 135                 140

Gly Ser Leu Tyr Phe Thr Glu Met Asp Thr Asp Gly Gly Leu Ala Lys
        145                 150                 155

Phe Pro Asp Asn Asp Ala Gly Ala Lys Phe Gly Thr Gly Tyr Cys Asp
    160                 165                 170

Ala Gln Cys Pro His Glu Val Lys Trp Gln Asn Gly Glu Ala Asn Met
175                 180                 185                 190

Leu Asp Trp Phe Pro Ile Ser Asn Asp Glu Arg Ala Trp Arg Gly Lys
                195                 200                 205

Tyr Gly Ala Cys Cys Thr Gln Ile Asp Leu Trp Glu Ala Asn Gln Tyr
            210                 215                 220

Ser Ala Ala Phe Thr Pro His Pro Cys Val Glu Lys Val Arg Cys Glu
        225                 230                 235

Asn Val Val Asp Cys Gly Asp Trp Ser Asn Arg Tyr Asp Gly Tyr Cys
    240                 245                 250

Asp Lys Asp Gly Cys Asp Tyr Asn Pro Tyr Arg Leu Gly Asp Pro Ser
255                 260                 265                 270

Phe Leu Gly Pro Gly Lys Ala Val Asp Thr Thr Gln Lys Ile Thr Val
                275                 280                 285

Ile Thr Gln Phe Ile Thr Asp Asp Asn Thr Pro Asn Gly Asn Leu Val
            290                 295                 300

Glu Ile Arg Arg Ile Phe Arg Gln Asn Gly Ile Ile Ile Gln Asn Ala
        305                 310                 315

Arg Val Asn Val Pro Gly Ile Pro Pro Tyr Asp Ser Ile Thr Asp Asp
    320                 325                 330

Phe Cys Ser Thr Gln Lys Thr Ala Phe Asn Asp Gln Asn Tyr Phe Ala
335                 340                 345                 350

Ser Leu Gly Gly Leu Gly Gln Val Gly His Gly Met Asp Asn Gly Leu
                355                 360                 365

Val Leu Ala Met Ser Leu Leu Asp Asp Pro Asp Arg Gln Leu Leu Trp
            370                 375                 380

Leu Asp Ser Thr Tyr Pro Pro Asp Arg Asp Ala Ala Glu Pro Gly Val
        385                 390                 395

Thr Arg Gly Thr Cys Ala Thr Ala Ser Gly Lys Pro Val Asp Leu Glu
    400                 405                 410

Ala Glu Ser Pro Asn Ala Ser Val Met Phe Ser Asn Ile Arg Tyr Gly
415                 420                 425                 430

Asp Ile Gly Ser Thr Tyr Pro Met Pro Gly Ser Gly Ser Thr Cys Ala
                435                 440                 445
```

```
Cys


<210> SEQ ID NO 3
<211> LENGTH: 1572
<212> TYPE: DNA
<213> ORGANISM: Hohenbuehelia mastrucata
<220> FEATURE:
<221> NAME/KEY: CDS
<222> LOCATION: (1)..(211)
<220> FEATURE:
<221> NAME/KEY: sig_peptide
<222> LOCATION: (1)..(54)
<220> FEATURE:
<221> NAME/KEY: mat_peptide
<222> LOCATION: (55)..()
<220> FEATURE:
<221> NAME/KEY: Intron
<222> LOCATION: (212)..(263)
<220> FEATURE:
<221> NAME/KEY: CDS
<222> LOCATION: (264)..(664)
<220> FEATURE:
<221> NAME/KEY: Intron
<222> LOCATION: (665)..(722)
<220> FEATURE:
<221> NAME/KEY: CDS
<222> LOCATION: (723)..(1472)

<400> SEQUENCE: 3

atg ttc cct gta gct act cta gtc gcc ttt atc ttt act gct gtg gcg       48
Met Phe Pro Val Ala Thr Leu Val Ala Phe Ile Phe Thr Ala Val Ala
            -15                 -10                 -5

caa gcc cag cag att ggg acc aac aca ctc gaa aca cat cca cct ctc       96
Gln Ala Gln Gln Ile Gly Thr Asn Thr Leu Glu Thr His Pro Pro Leu
    -1  1               5                   10

agc att caa tcg tgt acc aag aca ggc ggt tgt cag act caa cag aga      144
Ser Ile Gln Ser Cys Thr Lys Thr Gly Gly Cys Gln Thr Gln Gln Arg
15                  20                  25                  30

tcc atc gtg ctt gac gcc aac tgg cgg tgg ctg cac aac aac ggc ggt      192
Ser Ile Val Leu Asp Ala Asn Trp Arg Trp Leu His Asn Asn Gly Gly
                35                  40                  45

ttc acc aac tgt tat act g gtatgttacg ttcgatcttc ggtttgaccg          241
Phe Thr Asn Cys Tyr Thr
            50

agctttgctc accgtgccgc ag gg  aac act tgg gat gcg acg ctc tgt ccg     292
                         Gly Asn Thr Trp Asp Ala Thr Leu Cys Pro
                                 55                  60

gat cca gcc aca tgt gcc gcc aac tgt gcg ctg gac ggt gca gac tac      340
Asp Pro Ala Thr Cys Ala Ala Asn Cys Ala Leu Asp Gly Ala Asp Tyr
        65                  70                  75

gcc ggc act tat ggc atc acg aca agc ggc aac gct tta tcg ttg aaa      388
Ala Gly Thr Tyr Gly Ile Thr Thr Ser Gly Asn Ala Leu Ser Leu Lys
    80                  85                  90

ttc gta act cag agc gcc cag aaa aac gtc ggc tca cgg gtt tac ctt      436
Phe Val Thr Gln Ser Ala Gln Lys Asn Val Gly Ser Arg Val Tyr Leu
95                  100                 105                 110

atg gcc gat gaa acg cac tac cag act ttc aat ctc aaa aac aag gag      484
Met Ala Asp Glu Thr His Tyr Gln Thr Phe Asn Leu Lys Asn Lys Glu
                115                 120                 125

ttc acc ttc gac atc gat atg tca cag ctt ccc tgc ggt ctc aac ggc      532
Phe Thr Phe Asp Ile Asp Met Ser Gln Leu Pro Cys Gly Leu Asn Gly
            130                 135                 140

gcg ctg tac ttc tct cag atg ccc gca gat ggc ggt gtt tct cag ttt      580
Ala Leu Tyr Phe Ser Gln Met Pro Ala Asp Gly Gly Val Ser Gln Phe
        145                 150                 155
```

```
ccg agc aac aaa gct ggg gct aaa tac ggt act ggc tac tgt gac tcg      628
Pro Ser Asn Lys Ala Gly Ala Lys Tyr Gly Thr Gly Tyr Cys Asp Ser
    160                 165                 170

cag tgt ccg cac gac atc aag ttc att agt ggc gag gtgagccttc           674
Gln Cys Pro His Asp Ile Lys Phe Ile Ser Gly Glu
175                 180                 185

cttcaatcga gtaatggcaa aatacacgcc taaagcgccc tcgtgcag gct aat att     731
                                                     Ala Asn Ile

ctc ggc tgg aca ccg tca gcc agt gac ccc aac gcc ggt gcc ggg cag      779
Leu Gly Trp Thr Pro Ser Ala Ser Asp Pro Asn Ala Gly Ala Gly Gln
190                 195                 200                 205

atg ggt tcc tgc tgc aac gag atg gat att tgg gaa gcc aac tcc aat      827
Met Gly Ser Cys Cys Asn Glu Met Asp Ile Trp Glu Ala Asn Ser Asn
                210                 215                 220

gct gct gcc ttc act cct cac ccc tgc acc tcg caa att cgt tgc acc      875
Ala Ala Ala Phe Thr Pro His Pro Cys Thr Ser Gln Ile Arg Cys Thr
            225                 230                 235

tct cca acg cag tgc ggt gac gga gat aac cgt gct acc ggc gtg tgc      923
Ser Pro Thr Gln Cys Gly Asp Gly Asp Asn Arg Ala Thr Gly Val Cys
        240                 245                 250

gac aag gac ggt tgt gac ttc aac tcc ttc cgc atg ggc gac cag tcg      971
Asp Lys Asp Gly Cys Asp Phe Asn Ser Phe Arg Met Gly Asp Gln Ser
    255                 260                 265

ttc ctt ggc cct ggc aag acc gtc aac acc aat tcg aaa ttc acc gtc     1019
Phe Leu Gly Pro Gly Lys Thr Val Asn Thr Asn Ser Lys Phe Thr Val
270                 275                 280                 285

gtc aca caa ttc ctc acc gcc gac aac acc acc act ggc acg cta cgc     1067
Val Thr Gln Phe Leu Thr Ala Asp Asn Thr Thr Thr Gly Thr Leu Arg
                290                 295                 300

gaa atc cgt cgg ctc tac gtc cag aac ggc aag gtc atc cag aac tcc     1115
Glu Ile Arg Arg Leu Tyr Val Gln Asn Gly Lys Val Ile Gln Asn Ser
            305                 310                 315

aaa acg act atc ccc ggc atg caa gcg ttc gac tcg atc act gat cag     1163
Lys Thr Thr Ile Pro Gly Met Gln Ala Phe Asp Ser Ile Thr Asp Gln
        320                 325                 330

ttc tgt acg gcc cag aag act gcg ttc ggc gac acg aat tcg ttt tct     1211
Phe Cys Thr Ala Gln Lys Thr Ala Phe Gly Asp Thr Asn Ser Phe Ser
    335                 340                 345

gct cac gga ggt ctc gct gcc atg ggc tct gcc ttt gat aag ggc atg     1259
Ala His Gly Gly Leu Ala Ala Met Gly Ser Ala Phe Asp Lys Gly Met
350                 355                 360                 365

gtc ttg gtt atg agc atc tgg gat gac cac gaa gcc aac atg ctc tgg     1307
Val Leu Val Met Ser Ile Trp Asp Asp His Glu Ala Asn Met Leu Trp
                370                 375                 380

ctc gac agc gac ttc ccc aca acc aag tcg gcg tct act ccg ggt gtt     1355
Leu Asp Ser Asp Phe Pro Thr Thr Lys Ser Ala Ser Thr Pro Gly Val
            385                 390                 395

gct cgc ggc aca tgc gcg acc aat tcc ggt gtc ccc gct acc gtc gag     1403
Ala Arg Gly Thr Cys Ala Thr Asn Ser Gly Val Pro Ala Thr Val Glu
        400                 405                 410

tcg caa tcg ccg ggc gcg acc gtt gtc ttt tcg aac atc aag ttc ggt     1451
Ser Gln Ser Pro Gly Ala Thr Val Val Phe Ser Asn Ile Lys Phe Gly
    415                 420                 425

gac att ggc tcc act ttt tct tagtgaagta cgttcattgc tttacattta        1502
Asp Ile Gly Ser Thr Phe Ser
430                 435

gtttcgtttc tgacggactt gattaggctc aactcattgt cctcgacggg ccaacgaaaa   1562

atggtccgtt                                                          1572
```

```
<210> SEQ ID NO 4
<211> LENGTH: 454
<212> TYPE: PRT
<213> ORGANISM: Hohenbuehelia mastrucata

<400> SEQUENCE: 4

Met Phe Pro Val Ala Thr Leu Val Ala Phe Ile Phe Thr Ala Val Ala
            -15                 -10                 -5

Gln Ala Gln Gln Ile Gly Thr Asn Thr Leu Glu Thr His Pro Pro Leu
    -1  1               5                   10

Ser Ile Gln Ser Cys Thr Lys Thr Gly Gly Cys Gln Thr Gln Gln Arg
15                  20                  25                  30

Ser Ile Val Leu Asp Ala Asn Trp Arg Trp Leu His Asn Asn Gly Gly
                35                  40                  45

Phe Thr Asn Cys Tyr Thr Gly Asn Thr Trp Asp Ala Thr Leu Cys Pro
            50                  55                  60

Asp Pro Ala Thr Cys Ala Ala Asn Cys Ala Leu Asp Gly Ala Asp Tyr
        65                  70                  75

Ala Gly Thr Tyr Gly Ile Thr Thr Ser Gly Asn Ala Leu Ser Leu Lys
    80                  85                  90

Phe Val Thr Gln Ser Ala Gln Lys Asn Val Gly Ser Arg Val Tyr Leu
95                  100                 105                 110

Met Ala Asp Glu Thr His Tyr Gln Thr Phe Asn Leu Lys Asn Lys Glu
                115                 120                 125

Phe Thr Phe Asp Ile Asp Met Ser Gln Leu Pro Cys Gly Leu Asn Gly
            130                 135                 140

Ala Leu Tyr Phe Ser Gln Met Pro Ala Asp Gly Gly Val Ser Gln Phe
        145                 150                 155

Pro Ser Asn Lys Ala Gly Ala Lys Tyr Gly Thr Gly Tyr Cys Asp Ser
    160                 165                 170

Gln Cys Pro His Asp Ile Lys Phe Ile Ser Gly Glu Ala Asn Ile Leu
175                 180                 185                 190

Gly Trp Thr Pro Ser Ala Ser Asp Pro Asn Ala Gly Ala Gly Gln Met
                195                 200                 205

Gly Ser Cys Cys Asn Glu Met Asp Ile Trp Glu Ala Asn Ser Asn Ala
            210                 215                 220

Ala Ala Phe Thr Pro His Pro Cys Thr Ser Gln Ile Arg Cys Thr Ser
        225                 230                 235

Pro Thr Gln Cys Gly Asp Gly Asp Asn Arg Ala Thr Gly Val Cys Asp
    240                 245                 250

Lys Asp Gly Cys Asp Phe Asn Ser Phe Arg Met Gly Asp Gln Ser Phe
255                 260                 265                 270

Leu Gly Pro Gly Lys Thr Val Asn Thr Asn Ser Lys Phe Thr Val Val
                275                 280                 285

Thr Gln Phe Leu Thr Ala Asp Asn Thr Thr Thr Gly Thr Leu Arg Glu
            290                 295                 300

Ile Arg Arg Leu Tyr Val Gln Asn Gly Lys Val Ile Gln Asn Ser Lys
        305                 310                 315

Thr Thr Ile Pro Gly Met Gln Ala Phe Asp Ser Ile Thr Asp Gln Phe
    320                 325                 330

Cys Thr Ala Gln Lys Thr Ala Phe Gly Asp Thr Asn Ser Phe Ser Ala
335                 340                 345                 350

His Gly Gly Leu Ala Ala Met Gly Ser Ala Phe Asp Lys Gly Met Val
```

```
                355                 360                 365

Leu Val Met Ser Ile Trp Asp Asp His Glu Ala Asn Met Leu Trp Leu
            370                 375                 380

Asp Ser Asp Phe Pro Thr Thr Lys Ser Ala Ser Thr Pro Gly Val Ala
        385                 390                 395

Arg Gly Thr Cys Ala Thr Asn Ser Gly Val Pro Ala Thr Val Glu Ser
    400                 405                 410

Gln Ser Pro Gly Ala Thr Val Val Phe Ser Asn Ile Lys Phe Gly Asp
415                 420                 425                 430

Ile Gly Ser Thr Phe Ser
                435


<210> SEQ ID NO 5
<211> LENGTH: 1492
<212> TYPE: DNA
<213> ORGANISM: Hohenbuehelia mastrucata
<220> FEATURE:
<221> NAME/KEY: CDS
<222> LOCATION: (1)..(211)
<220> FEATURE:
<221> NAME/KEY: sig_peptide
<222> LOCATION: (1)..(54)
<220> FEATURE:
<221> NAME/KEY: mat_peptide
<222> LOCATION: (55)..()
<220> FEATURE:
<221> NAME/KEY: Intron
<222> LOCATION: (212)..(277)
<220> FEATURE:
<221> NAME/KEY: CDS
<222> LOCATION: (278)..(678)
<220> FEATURE:
<221> NAME/KEY: Intron
<222> LOCATION: (679)..(742)
<220> FEATURE:
<221> NAME/KEY: CDS
<222> LOCATION: (743)..(1489)

<400> SEQUENCE: 5

atg ttc cgc gcc gca gct ctt ttc gct tac acc ctc ctc gct gtt gtt       48
Met Phe Arg Ala Ala Ala Leu Phe Ala Tyr Thr Leu Leu Ala Val Val
            -15                 -10                 -5

cga gcc cag caa gtt ggc acg aac acg gcc gag acc cac cct gcg ctg       96
Arg Ala Gln Gln Val Gly Thr Asn Thr Ala Glu Thr His Pro Ala Leu
    -1  1               5                   10

agc gtg cag caa tgc acg gcg ggc ggt tcc tgc aca acc cag gcg cgc      144
Ser Val Gln Gln Cys Thr Ala Gly Gly Ser Cys Thr Thr Gln Ala Arg
15                  20                  25                  30

tcc atc gtc ctt gat tcc aac tgg cgc tgg ctg cac acg acc acc ggg      192
Ser Ile Val Leu Asp Ser Asn Trp Arg Trp Leu His Thr Thr Thr Gly
                35                  40                  45

ttt acc aac tgc tac acc g gtacttcaga catttgtctt tcacttctcc           241
Phe Thr Asn Cys Tyr Thr
            50

tcctcctatg cttatgcgtg taatcctttt cttcag gc  aac act tgg gac gca      294
                                        Gly Asn Thr Trp Asp Ala
                                                    55

tct ctg tgc cca gat ggc gct aca tgt gcg gcc aac tgt gca ctc gat      342
Ser Leu Cys Pro Asp Gly Ala Thr Cys Ala Ala Asn Cys Ala Leu Asp
    60                  65                  70

ggt gcg gac tac tcc ggc aca tac ggc atc agc acg tct ggc aac gcc      390
Gly Ala Asp Tyr Ser Gly Thr Tyr Gly Ile Ser Thr Ser Gly Asn Ala
75                  80                  85                  90

ctt acg ctc aag ttc atc acg caa agc cag cag aag aac atc ggc tcg      438
```

```
Leu Thr Leu Lys Phe Ile Thr Gln Ser Gln Gln Lys Asn Ile Gly Ser
                95                  100                 105

cgc gtc tac ctc ctc gag tcc gac tcg tcc tac cag atc ttc aac ctc      486
Arg Val Tyr Leu Leu Glu Ser Asp Ser Ser Tyr Gln Ile Phe Asn Leu
            110                 115                 120

aag aac cag gag ttc acc ttt gac atc gac atg tct aac ctc cca tgc      534
Lys Asn Gln Glu Phe Thr Phe Asp Ile Asp Met Ser Asn Leu Pro Cys
        125                 130                 135

ggt ctc aac ggt gct ctg tac ttc tcg cag atg ccc aag gac gga ggc      582
Gly Leu Asn Gly Ala Leu Tyr Phe Ser Gln Met Pro Lys Asp Gly Gly
    140                 145                 150

atg tcc cag ttc ccc acc aac aaa gcc ggt gcc aag tat gga act ggt      630
Met Ser Gln Phe Pro Thr Asn Lys Ala Gly Ala Lys Tyr Gly Thr Gly
155                 160                 165                 170

tac tgc gac tcg cag tgc ccg cat gac atc aag ttc atc aat ggc gag      678
Tyr Cys Asp Ser Gln Cys Pro His Asp Ile Lys Phe Ile Asn Gly Glu
                175                 180                 185

gtgcgctcaa ccttactcaa gtcaataaca tggatttgca ctgactgatg cgaatgttcg    738

acag gca aac gtt gag ggc tgg gca cca tcc ccc aat gac ccg aat gcg     787
     Ala Asn Val Glu Gly Trp Ala Pro Ser Pro Asn Asp Pro Asn Ala
                190                 195                 200

ggc acg ggc acc tac gga tcg tgc tgc cct gag atg gat gtc tgg gag      835
Gly Thr Gly Thr Tyr Gly Ser Cys Cys Pro Glu Met Asp Val Trp Glu
            205                 210                 215

gcc aac tcc atg gct gca gcg tac act ccc cac ccg tgc act gcc tca      883
Ala Asn Ser Met Ala Ala Ala Tyr Thr Pro His Pro Cys Thr Ala Ser
        220                 225                 230

gag cgt tgt gag ggc acc gcg tgc ggt gac ggt gat gag cgc tac gac      931
Glu Arg Cys Glu Gly Thr Ala Cys Gly Asp Gly Asp Glu Arg Tyr Asp
    235                 240                 245

ggc gtc tgc gac aag gac ggc tgc gac ttc aac tcg ttc cgc atg ggc      979
Gly Val Cys Asp Lys Asp Gly Cys Asp Phe Asn Ser Phe Arg Met Gly
250                 255                 260                 265

gac cag acc ttc ctc ggc cct ggc atg acc gtc gac acc aat tcc aag     1027
Asp Gln Thr Phe Leu Gly Pro Gly Met Thr Val Asp Thr Asn Ser Lys
                270                 275                 280

ttc acc gtc gtc acc cag ttc ctc acc gct gac aac acc acc acc ggc     1075
Phe Thr Val Val Thr Gln Phe Leu Thr Ala Asp Asn Thr Thr Thr Gly
            285                 290                 295

acc ctc tct gag atc cgt cgc ctc tac gtc cag aac ggc cag gtc atc     1123
Thr Leu Ser Glu Ile Arg Arg Leu Tyr Val Gln Asn Gly Gln Val Ile
        300                 305                 310

cag aac tcc aag gtc aac atc ccg ggc atg gac gcc tcc atg gac tcg     1171
Gln Asn Ser Lys Val Asn Ile Pro Gly Met Asp Ala Ser Met Asp Ser
    315                 320                 325

atc acc gac gag ttc tgc tcc gct cag aag acg gcc ttc ggt gac acc     1219
Ile Thr Asp Glu Phe Cys Ser Ala Gln Lys Thr Ala Phe Gly Asp Thr
330                 335                 340                 345

aac tcg ttc cag tcc aag ggt ggc ctc gca gcc atg gga gac gct ttc     1267
Asn Ser Phe Gln Ser Lys Gly Gly Leu Ala Ala Met Gly Asp Ala Phe
                350                 355                 360

gac gcc ggc atg gtt ctc gtc atg agt gtt tgg gac gac cac gca gtc     1315
Asp Ala Gly Met Val Leu Val Met Ser Val Trp Asp Asp His Ala Val
            365                 370                 375

aac atg ctc tgg ctc gac agt gac tac ccg acc gac aag gac ccg tcc     1363
Asn Met Leu Trp Leu Asp Ser Asp Tyr Pro Thr Asp Lys Asp Pro Ser
        380                 385                 390

gca ccc ggt gtt gct cgc ggt aac tgt gcg acc acc tct ggt gtc ccg     1411
Ala Pro Gly Val Ala Arg Gly Asn Cys Ala Thr Thr Ser Gly Val Pro
```

```
    395                 400                 405

act gac gtc gag agc tct gcc gcc agc gcc tcc gtc act ttc tcg aac     1459
Thr Asp Val Glu Ser Ser Ala Ala Ser Ala Ser Val Thr Phe Ser Asn
410                 415                 420                 425

atc aag ttc ggt gcc att ggc tcg acc ttt taa                         1492
Ile Lys Phe Gly Ala Ile Gly Ser Thr Phe
                430                 435


<210> SEQ ID NO 6
<211> LENGTH: 453
<212> TYPE: PRT
<213> ORGANISM: Hohenbuehelia mastrucata

<400> SEQUENCE: 6

Met Phe Arg Ala Ala Ala Leu Phe Ala Tyr Thr Leu Leu Ala Val Val
            -15                 -10                 -5

Arg Ala Gln Gln Val Gly Thr Asn Thr Ala Glu Thr His Pro Ala Leu
    -1  1               5                   10

Ser Val Gln Gln Cys Thr Ala Gly Gly Ser Cys Thr Thr Gln Ala Arg
15                  20                  25                  30

Ser Ile Val Leu Asp Ser Asn Trp Arg Trp Leu His Thr Thr Thr Gly
                35                  40                  45

Phe Thr Asn Cys Tyr Thr Gly Asn Thr Trp Asp Ala Ser Leu Cys Pro
            50                  55                  60

Asp Gly Ala Thr Cys Ala Ala Asn Cys Ala Leu Asp Gly Ala Asp Tyr
        65                  70                  75

Ser Gly Thr Tyr Gly Ile Ser Thr Ser Gly Asn Ala Leu Thr Leu Lys
    80                  85                  90

Phe Ile Thr Gln Ser Gln Gln Lys Asn Ile Gly Ser Arg Val Tyr Leu
95                  100                 105                 110

Leu Glu Ser Asp Ser Ser Tyr Gln Ile Phe Asn Leu Lys Asn Gln Glu
                115                 120                 125

Phe Thr Phe Asp Ile Asp Met Ser Asn Leu Pro Cys Gly Leu Asn Gly
            130                 135                 140

Ala Leu Tyr Phe Ser Gln Met Pro Lys Asp Gly Gly Met Ser Gln Phe
        145                 150                 155

Pro Thr Asn Lys Ala Gly Ala Lys Tyr Gly Thr Gly Tyr Cys Asp Ser
    160                 165                 170

Gln Cys Pro His Asp Ile Lys Phe Ile Asn Gly Glu Ala Asn Val Glu
175                 180                 185                 190

Gly Trp Ala Pro Ser Pro Asn Asp Pro Asn Ala Gly Thr Gly Thr Tyr
                195                 200                 205

Gly Ser Cys Cys Pro Glu Met Asp Val Trp Glu Ala Asn Ser Met Ala
            210                 215                 220

Ala Ala Tyr Thr Pro His Pro Cys Thr Ala Ser Glu Arg Cys Glu Gly
        225                 230                 235

Thr Ala Cys Gly Asp Gly Asp Glu Arg Tyr Asp Gly Val Cys Asp Lys
    240                 245                 250

Asp Gly Cys Asp Phe Asn Ser Phe Arg Met Gly Asp Gln Thr Phe Leu
255                 260                 265                 270

Gly Pro Gly Met Thr Val Asp Thr Asn Ser Lys Phe Thr Val Val Thr
                275                 280                 285

Gln Phe Leu Thr Ala Asp Asn Thr Thr Thr Gly Thr Leu Ser Glu Ile
            290                 295                 300

Arg Arg Leu Tyr Val Gln Asn Gly Gln Val Ile Gln Asn Ser Lys Val
```

```
        305                 310                 315

Asn Ile Pro Gly Met Asp Ala Ser Met Asp Ser Ile Thr Asp Glu Phe
    320                 325                 330

Cys Ser Ala Gln Lys Thr Ala Phe Gly Asp Thr Asn Ser Phe Gln Ser
335                 340                 345                 350

Lys Gly Gly Leu Ala Ala Met Gly Asp Ala Phe Asp Ala Gly Met Val
                355                 360                 365

Leu Val Met Ser Val Trp Asp Asp His Ala Val Asn Met Leu Trp Leu
            370                 375                 380

Asp Ser Asp Tyr Pro Thr Asp Lys Asp Pro Ser Ala Pro Gly Val Ala
        385                 390                 395

Arg Gly Asn Cys Ala Thr Thr Ser Gly Val Pro Thr Asp Val Glu Ser
    400                 405                 410

Ser Ala Ala Ser Ala Ser Val Thr Phe Ser Asn Ile Lys Phe Gly Ala
415                 420                 425                 430

Ile Gly Ser Thr Phe
                435


<210> SEQ ID NO 7
<211> LENGTH: 1496
<212> TYPE: DNA
<213> ORGANISM: Hohenbuehelia mastucata
<220> FEATURE:
<221> NAME/KEY: CDS
<222> LOCATION: (1)..(211)
<220> FEATURE:
<221> NAME/KEY: sig_peptide
<222> LOCATION: (1)..(54)
<220> FEATURE:
<221> NAME/KEY: mat_peptide
<222> LOCATION: (55)..()
<220> FEATURE:
<221> NAME/KEY: Intron
<222> LOCATION: (212)..(268)
<220> FEATURE:
<221> NAME/KEY: CDS
<222> LOCATION: (269)..(672)
<220> FEATURE:
<221> NAME/KEY: Intron
<222> LOCATION: (673)..(734)
<220> FEATURE:
<221> NAME/KEY: CDS
<222> LOCATION: (735)..(1493)

<400> SEQUENCE: 7

atg ttc cgc tca gta gct ctt gtc gct ttt tcg ctc ctc gct att gtt       48
Met Phe Arg Ser Val Ala Leu Val Ala Phe Ser Leu Leu Ala Ile Val
            -15                 -10                 -5

cac ggt caa caa gtc ggc acg ctg cag gct gag aca cac ccg aca gtc       96
His Gly Gln Gln Val Gly Thr Leu Gln Ala Glu Thr His Pro Thr Val
    -1  1               5                   10

acc atc cag aaa tgc acg aag ggt ggt agt tgc act acg cag caa cgc      144
Thr Ile Gln Lys Cys Thr Lys Gly Gly Ser Cys Thr Thr Gln Gln Arg
15                  20                  25                  30

tcg att gtg ctc gac tcg aat tgg cgg tgg tta cac aca aca tct ggc      192
Ser Ile Val Leu Asp Ser Asn Trp Arg Trp Leu His Thr Thr Ser Gly
                35                  40                  45

agc acc aat tgc tac aca g gtacgaggag catctcttgt tgtatctata           241
Ser Thr Asn Cys Tyr Thr
            50

tgttttgaga ctgattgcgt tcaatag ga  aac acc tgg gat act tct ctg tgc    294
                              Gly Asn Thr Trp Asp Thr Ser Leu Cys
                                      55                  60
```

```
ccc gac ggt gtc acc tgc gcc aag aat tgt gct ctc gat ggc gct gac      342
Pro Asp Gly Val Thr Cys Ala Lys Asn Cys Ala Leu Asp Gly Ala Asp
            65                  70                  75

tac gcc ggc act tac ggt att acg gct agc ggc aat gct gtc act ttt      390
Tyr Ala Gly Thr Tyr Gly Ile Thr Ala Ser Gly Asn Ala Val Thr Phe
        80                  85                  90

aag ttt gtg act cac ggc ccg tac tcc acc aac atc ggt gga cgc gcc      438
Lys Phe Val Thr His Gly Pro Tyr Ser Thr Asn Ile Gly Gly Arg Ala
    95                  100                 105

tac ctc ctc gag acc gac tcc aag tac cag atg ttc aat ctc aat aac      486
Tyr Leu Leu Glu Thr Asp Ser Lys Tyr Gln Met Phe Asn Leu Asn Asn
110                 115                 120                 125

caa gag ttc acc ttc gat gtc gac gtg tcg cag ctg ccc tgt ggt ctg      534
Gln Glu Phe Thr Phe Asp Val Asp Val Ser Gln Leu Pro Cys Gly Leu
                130                 135                 140

aac ggg gcg ctg tat ttc gtt cag atg gac gct gac ggc ggc atg gcg      582
Asn Gly Ala Leu Tyr Phe Val Gln Met Asp Ala Asp Gly Gly Met Ala
            145                 150                 155

aag tcc ccg aac aac aag gcc ggc gct aaa tac ggc acg ggc tac tgc      630
Lys Ser Pro Asn Asn Lys Ala Gly Ala Lys Tyr Gly Thr Gly Tyr Cys
        160                 165                 170

gac tcg caa tgc ccg cac gat atc aag ttc atc aac gga gag              672
Asp Ser Gln Cys Pro His Asp Ile Lys Phe Ile Asn Gly Glu
    175                 180                 185

gtaagtcttt tcgcactgca cccattgggc atacattctc atcttctccg tctgtactat    732

ag gcc aac gtt gct ggt tgg aca ccc tct ccc aac gat gcg aac gcc       779
   Ala Asn Val Ala Gly Trp Thr Pro Ser Pro Asn Asp Ala Asn Ala
           190                 195                 200

ggc aag ggc cag tac ggc acc tgt tgc agc gag atg gac atc tgg gag      827
Gly Lys Gly Gln Tyr Gly Thr Cys Cys Ser Glu Met Asp Ile Trp Glu
        205                 210                 215

gcg aac tcc atg gct gcc gcc tac act ccg cac gtc tgc acc gga tcg      875
Ala Asn Ser Met Ala Ala Ala Tyr Thr Pro His Val Cys Thr Gly Ser
    220                 225                 230

ggc ctg acg cgc tgc acg ggc aac gat tgc ggt gat ggc gac aac cgc      923
Gly Leu Thr Arg Cys Thr Gly Asn Asp Cys Gly Asp Gly Asp Asn Arg
235                 240                 245                 250

tac ggc ggc att tgc gac aag gac ggc tgc gac ttc aac tcg ttc cgc      971
Tyr Gly Gly Ile Cys Asp Lys Asp Gly Cys Asp Phe Asn Ser Phe Arg
                255                 260                 265

atg ggc gac aag agc ttc tac ggc aag ggc atg gcc gtc aac acc aac     1019
Met Gly Asp Lys Ser Phe Tyr Gly Lys Gly Met Ala Val Asn Thr Asn
            270                 275                 280

tcc aag ttc acc gtc gtc acc caa ttc ctc act aac aac aac agc acc     1067
Ser Lys Phe Thr Val Val Thr Gln Phe Leu Thr Asn Asn Asn Ser Thr
        285                 290                 295

tcg ggc acg ctc tcg gaa atc cgt cgc ttg tac gtg cag aac ggc aag     1115
Ser Gly Thr Leu Ser Glu Ile Arg Arg Leu Tyr Val Gln Asn Gly Lys
    300                 305                 310

gtc atc gca aac tca aag aca gcc atc tcc ggc atg tcc gcg tac gac     1163
Val Ile Ala Asn Ser Lys Thr Ala Ile Ser Gly Met Ser Ala Tyr Asp
315                 320                 325                 330

tct gtc acg gat tca ttc tgc aac gcg cag aag acc gcc ttc ggc gac     1211
Ser Val Thr Asp Ser Phe Cys Asn Ala Gln Lys Thr Ala Phe Gly Asp
                335                 340                 345

acc aac tcg ttc gag cag cgc ggc ggc ctc aaa gcc atg ggc cag gcc     1259
Thr Asn Ser Phe Glu Gln Arg Gly Gly Leu Lys Ala Met Gly Gln Ala
            350                 355                 360

ttc acc aag ggc atg acc ctc gtg atg agt att tgg gac gac cac gag     1307
```

```
Phe Thr Lys Gly Met Thr Leu Val Met Ser Ile Trp Asp Asp His Glu
        365                 370                 375

gca aac atg ctc tgg ctc gat agc aac tac ccg ctg acc aaa tcc gcg      1355
Ala Asn Met Leu Trp Leu Asp Ser Asn Tyr Pro Leu Thr Lys Ser Ala
    380                 385                 390

tcc acc cct ggt gtc gct cgt ggc act tgc gcc aca aca tcc ggc aaa      1403
Ser Thr Pro Gly Val Ala Arg Gly Thr Cys Ala Thr Thr Ser Gly Lys
395                 400                 405                 410

ccc act gat gtc gag tct cag agc ccg aac gcc caa gtc atc tac tcc      1451
Pro Thr Asp Val Glu Ser Gln Ser Pro Asn Ala Gln Val Ile Tyr Ser
                415                 420                 425

aac atc aag tac gga gat atc ggt tcg acg ttc cag gca tcg taa          1496
Asn Ile Lys Tyr Gly Asp Ile Gly Ser Thr Phe Gln Ala Ser
            430                 435                 440


<210> SEQ ID NO 8
<211> LENGTH: 458
<212> TYPE: PRT
<213> ORGANISM: Hohenbuehelia mastucata

<400> SEQUENCE: 8

Met Phe Arg Ser Val Ala Leu Val Ala Phe Ser Leu Leu Ala Ile Val
            -15                 -10                 -5

His Gly Gln Gln Val Gly Thr Leu Gln Ala Glu Thr His Pro Thr Val
    -1  1               5                   10

Thr Ile Gln Lys Cys Thr Lys Gly Gly Ser Cys Thr Thr Gln Gln Arg
15                  20                  25                  30

Ser Ile Val Leu Asp Ser Asn Trp Arg Trp Leu His Thr Thr Ser Gly
                35                  40                  45

Ser Thr Asn Cys Tyr Thr Gly Asn Thr Trp Asp Thr Ser Leu Cys Pro
            50                  55                  60

Asp Gly Val Thr Cys Ala Lys Asn Cys Ala Leu Asp Gly Ala Asp Tyr
        65                  70                  75

Ala Gly Thr Tyr Gly Ile Thr Ala Ser Gly Asn Ala Val Thr Phe Lys
    80                  85                  90

Phe Val Thr His Gly Pro Tyr Ser Thr Asn Ile Gly Gly Arg Ala Tyr
95                  100                 105                 110

Leu Leu Glu Thr Asp Ser Lys Tyr Gln Met Phe Asn Leu Asn Asn Gln
                115                 120                 125

Glu Phe Thr Phe Asp Val Asp Val Ser Gln Leu Pro Cys Gly Leu Asn
            130                 135                 140

Gly Ala Leu Tyr Phe Val Gln Met Asp Ala Asp Gly Gly Met Ala Lys
        145                 150                 155

Ser Pro Asn Asn Lys Ala Gly Ala Lys Tyr Gly Thr Gly Tyr Cys Asp
    160                 165                 170

Ser Gln Cys Pro His Asp Ile Lys Phe Ile Asn Gly Glu Ala Asn Val
175                 180                 185                 190

Ala Gly Trp Thr Pro Ser Pro Asn Asp Ala Asn Ala Gly Lys Gly Gln
                195                 200                 205

Tyr Gly Thr Cys Cys Ser Glu Met Asp Ile Trp Glu Ala Asn Ser Met
            210                 215                 220

Ala Ala Ala Tyr Thr Pro His Val Cys Thr Gly Ser Gly Leu Thr Arg
        225                 230                 235

Cys Thr Gly Asn Asp Cys Gly Asp Gly Asp Asn Arg Tyr Gly Gly Ile
    240                 245                 250

Cys Asp Lys Asp Gly Cys Asp Phe Asn Ser Phe Arg Met Gly Asp Lys
```

```
255                 260                 265                 270

Ser Phe Tyr Gly Lys Gly Met Ala Val Asn Thr Asn Ser Lys Phe Thr
                275                 280                 285

Val Val Thr Gln Phe Leu Thr Asn Asn Asn Ser Thr Ser Gly Thr Leu
            290                 295                 300

Ser Glu Ile Arg Arg Leu Tyr Val Gln Asn Gly Lys Val Ile Ala Asn
        305                 310                 315

Ser Lys Thr Ala Ile Ser Gly Met Ser Ala Tyr Asp Ser Val Thr Asp
    320                 325                 330

Ser Phe Cys Asn Ala Gln Lys Thr Ala Phe Gly Asp Thr Asn Ser Phe
335                 340                 345                 350

Glu Gln Arg Gly Gly Leu Lys Ala Met Gly Gln Ala Phe Thr Lys Gly
                355                 360                 365

Met Thr Leu Val Met Ser Ile Trp Asp Asp His Glu Ala Asn Met Leu
            370                 375                 380

Trp Leu Asp Ser Asn Tyr Pro Leu Thr Lys Ser Ala Ser Thr Pro Gly
        385                 390                 395

Val Ala Arg Gly Thr Cys Ala Thr Thr Ser Gly Lys Pro Thr Asp Val
    400                 405                 410

Glu Ser Gln Ser Pro Asn Ala Gln Val Ile Tyr Ser Asn Ile Lys Tyr
415                 420                 425                 430

Gly Asp Ile Gly Ser Thr Phe Gln Ala Ser
                435                 440
```

<210> SEQ ID NO 9
<211> LENGTH: 1789
<212> TYPE: DNA
<213> ORGANISM: Hohenbuehelia mastrucata
<220> FEATURE:
<221> NAME/KEY: CDS
<222> LOCATION: (1)..(190)
<220> FEATURE:
<221> NAME/KEY: sig_peptide
<222> LOCATION: (1)..(54)
<220> FEATURE:
<221> NAME/KEY: mat_peptide
<222> LOCATION: (55)..()
<220> FEATURE:
<221> NAME/KEY: Intron
<222> LOCATION: (191)..(254)
<220> FEATURE:
<221> NAME/KEY: CDS
<222> LOCATION: (255)..(604)
<220> FEATURE:
<221> NAME/KEY: Intron
<222> LOCATION: (605)..(657)
<220> FEATURE:
<221> NAME/KEY: CDS
<222> LOCATION: (658)..(729)
<220> FEATURE:
<221> NAME/KEY: Intron
<222> LOCATION: (730)..(786)
<220> FEATURE:
<221> NAME/KEY: CDS
<222> LOCATION: (787)..(1711)
<220> FEATURE:
<221> NAME/KEY: Intron
<222> LOCATION: (1712)..(1766)
<220> FEATURE:
<221> NAME/KEY: CDS
<222> LOCATION: (1767)..(1786)

<400> SEQUENCE: 9

```
atg ttc cgc tcc gct gct ctc att gct ttc acc ttc gcg gct gtc gtc       48
Met Phe Arg Ser Ala Ala Leu Ile Ala Phe Thr Phe Ala Ala Val Val
            -15                 -10                 -5
```

```
ctc ggt caa cag gtc ggc acc ttg acg gca gag aac cac cct tct ctc       96
Leu Gly Gln Gln Val Gly Thr Leu Thr Ala Glu Asn His Pro Ser Leu
    -1  1               5                  10

cag gtc tct cag tgc acc aag tct ggc ggt tgc acg acc acc act aag      144
Gln Val Ser Gln Cys Thr Lys Ser Gly Gly Cys Thr Thr Thr Thr Lys
15                  20                  25                  30

tcc gtc gtg ctt gac gcc aac tgg cgc tgg ctc cac agc acc tcc g        190
Ser Val Val Leu Asp Ala Asn Trp Arg Trp Leu His Ser Thr Ser
                35                  40                  45

gtacgttttc tgtcacacca atttctggtg agccgctaaa atgaccaaat tacaatttct    250

acag gc  tcg aac aac tgc tac acc ggt aac acc tgg gac gcc acc ctg     298
     Gly Ser Asn Asn Cys Tyr Thr Gly Asn Thr Trp Asp Ala Thr Leu
                     50                  55                  60

tgc ccc gac gcc gcc act tgc gcc act aac tgt gcg ctc gat ggt gcc      346
Cys Pro Asp Ala Ala Thr Cys Ala Thr Asn Cys Ala Leu Asp Gly Ala
                65                  70                  75

gac tac tct ggc aca tac gga atc acc act tcc ggc aac gcg ttg acc      394
Asp Tyr Ser Gly Thr Tyr Gly Ile Thr Thr Ser Gly Asn Ala Leu Thr
            80                  85                  90

atg aag ttc gtc act caa agc gcc cag aag aac atc ggt tcc cgt gtc      442
Met Lys Phe Val Thr Gln Ser Ala Gln Lys Asn Ile Gly Ser Arg Val
        95                  100                 105

tac ctt atg gat gac gcc agc aca tac aag atg ttc aac ctc aag aac      490
Tyr Leu Met Asp Asp Ala Ser Thr Tyr Lys Met Phe Asn Leu Lys Asn
    110                 115                 120

cag gag ttc acc ttc gac gtc gac atg tcc ggg ctt ccc tgc gga ctt      538
Gln Glu Phe Thr Phe Asp Val Asp Met Ser Gly Leu Pro Cys Gly Leu
125                 130                 135                 140

aac ggt gct ttg tac ttc tct gag atg gcg aag gat ggt ggc atg tcg      586
Asn Gly Ala Leu Tyr Phe Ser Glu Met Ala Lys Asp Gly Gly Met Ser
                145                 150                 155

act cag cca tcc aac aag gtacgaaccc ctgaagaata cgacacaatg             634
Thr Gln Pro Ser Asn Lys
            160

ccattctgat attgctccct cag gct ggc gcc aaa tac gga act gga tac tgt    687
                          Ala Gly Ala Lys Tyr Gly Thr Gly Tyr Cys
                                  165                 170

gac tcg cag tgc ccc cac gac atc aag ttc att ggt ggc aag              729
Asp Ser Gln Cys Pro His Asp Ile Lys Phe Ile Gly Gly Lys
        175                 180                 185

gttagtagac cgttttcctg attgcggggc accgatcctc atgaaatgtt tctctag       786

gcc aac gtc gcg ggc tgg gaa gga tcc ccc aac gac ccc aac gcc ggc      834
Ala Asn Val Ala Gly Trp Glu Gly Ser Pro Asn Asp Pro Asn Ala Gly
            190                 195                 200

agt ggt acc atg ggt gcc tgc tgc tcc gag atg gac atc tgg gag gcc      882
Ser Gly Thr Met Gly Ala Cys Cys Ser Glu Met Asp Ile Trp Glu Ala
        205                 210                 215

aac acc atg gct gct gcc tac acc ccc cac cct tgc acg acc act ggt      930
Asn Thr Met Ala Ala Ala Tyr Thr Pro His Pro Cys Thr Thr Thr Gly
    220                 225                 230

ctc ctc gcc tgc act ggc acc cag tgc ggt gac gac gac gac cgt tac      978
Leu Leu Ala Cys Thr Gly Thr Gln Cys Gly Asp Asp Asp Asp Arg Tyr
235                 240                 245                 250

aac ggt gtc tgc gac aag gac ggt tgt gac ttc aac tcg ttc cgc atg     1026
Asn Gly Val Cys Asp Lys Asp Gly Cys Asp Phe Asn Ser Phe Arg Met
                255                 260                 265

ggc gac aag act ttc ctc ggc aag ggt aag act gtc gac acc acc aag     1074
Gly Asp Lys Thr Phe Leu Gly Lys Gly Lys Thr Val Asp Thr Thr Lys
```

```
            270                 275                 280

aag atc acc gtc gtc act cag ttc atc acc tct gac ggc act gcc aac      1122
Lys Ile Thr Val Val Thr Gln Phe Ile Thr Ser Asp Gly Thr Ala Asn
        285                 290                 295

ggc gac ctc act gag atc cgc cgt ctt tac gtc cag aac ggc aag gtc      1170
Gly Asp Leu Thr Glu Ile Arg Arg Leu Tyr Val Gln Asn Gly Lys Val
    300                 305                 310

atc caa aac agc atg tcg agc atc cca ggc acc acg gcc gtc aac tcg      1218
Ile Gln Asn Ser Met Ser Ser Ile Pro Gly Thr Thr Ala Val Asn Ser
315                 320                 325                 330

ctc act gac gcg tcc tgc act gct cag aag tcc gtt ttc ggt gac acg      1266
Leu Thr Asp Ala Ser Cys Thr Ala Gln Lys Ser Val Phe Gly Asp Thr
                335                 340                 345

aac tcg ttc tcg tcc aag ggt gga atg aag gcg atg ggc gac tcc ttc      1314
Asn Ser Phe Ser Ser Lys Gly Gly Met Lys Ala Met Gly Asp Ser Phe
            350                 355                 360

cag cgc ggc atg gtc ctc gtc atg tct atc tgg gac gac cac gct gtc      1362
Gln Arg Gly Met Val Leu Val Met Ser Ile Trp Asp Asp His Ala Val
        365                 370                 375

aac atg ctc tgg ctc gac tcc gac tac ccc acc gac gct gac ccc agc      1410
Asn Met Leu Trp Leu Asp Ser Asp Tyr Pro Thr Asp Ala Asp Pro Ser
    380                 385                 390

agc ccc ggt gtc gct cgc gga gag tgt gcc acc acc tcc ggc aag ccc      1458
Ser Pro Gly Val Ala Arg Gly Glu Cys Ala Thr Thr Ser Gly Lys Pro
395                 400                 405                 410

acc gac gtt gag gcc aac cct gcg ggc atc caa gtc atc tac tcc aac      1506
Thr Asp Val Glu Ala Asn Pro Ala Gly Ile Gln Val Ile Tyr Ser Asn
                415                 420                 425

atc aag ttc ggt gac att ggc tcg acc tac act ggc acc gca ggc ggc      1554
Ile Lys Phe Gly Asp Ile Gly Ser Thr Tyr Thr Gly Thr Ala Gly Gly
            430                 435                 440

agt ccg agc ggc ccg agc tcc acc act ggc ccc agc agc acc gct gcc      1602
Ser Pro Ser Gly Pro Ser Ser Thr Thr Gly Pro Ser Ser Thr Ala Ala
        445                 450                 455

ccg ccc acg aac acc gct act gct ggc ctc tac gcc cag tgc ggt gga      1650
Pro Pro Thr Asn Thr Ala Thr Ala Gly Leu Tyr Ala Gln Cys Gly Gly
    460                 465                 470

att ggc ttc agc ggc ccg act gcc tgc gtg tct ggc gcg acc tgc acg      1698
Ile Gly Phe Ser Gly Pro Thr Ala Cys Val Ser Gly Ala Thr Cys Thr
475                 480                 485                 490

aag ctc aac gac t gtgcgtttat tttgtaaccc tcatgcgcct tgtcgatact        1751
Lys Leu Asn Asp

gacattccct tgtag ac  tac tct cag tgc ctc ccc taa                     1789
                 Tyr Tyr Ser Gln Cys Leu Pro
                 495                 500


<210> SEQ ID NO 10
<211> LENGTH: 519
<212> TYPE: PRT
<213> ORGANISM: Hohenbuehelia mastrucata

<400> SEQUENCE: 10

Met Phe Arg Ser Ala Ala Leu Ile Ala Phe Thr Phe Ala Ala Val Val
            -15                 -10                 -5

Leu Gly Gln Gln Val Gly Thr Leu Thr Ala Glu Asn His Pro Ser Leu
    -1  1               5                   10

Gln Val Ser Gln Cys Thr Lys Ser Gly Gly Cys Thr Thr Thr Thr Lys
15                  20                  25                  30

Ser Val Val Leu Asp Ala Asn Trp Arg Trp Leu His Ser Thr Ser Gly
```

-continued

```
                35                  40                  45

Ser Asn Asn Cys Tyr Thr Gly Asn Thr Trp Asp Ala Thr Leu Cys Pro
            50                  55                  60

Asp Ala Ala Thr Cys Ala Thr Asn Cys Ala Leu Asp Gly Ala Asp Tyr
        65                  70                  75

Ser Gly Thr Tyr Gly Ile Thr Thr Ser Gly Asn Ala Leu Thr Met Lys
    80                  85                  90

Phe Val Thr Gln Ser Ala Gln Lys Asn Ile Gly Ser Arg Val Tyr Leu
95                  100                 105                 110

Met Asp Asp Ala Ser Thr Tyr Lys Met Phe Asn Leu Lys Asn Gln Glu
                115                 120                 125

Phe Thr Phe Asp Val Asp Met Ser Gly Leu Pro Cys Gly Leu Asn Gly
            130                 135                 140

Ala Leu Tyr Phe Ser Glu Met Ala Lys Asp Gly Gly Met Ser Thr Gln
        145                 150                 155

Pro Ser Asn Lys Ala Gly Ala Lys Tyr Gly Thr Gly Tyr Cys Asp Ser
    160                 165                 170

Gln Cys Pro His Asp Ile Lys Phe Ile Gly Gly Lys Ala Asn Val Ala
175                 180                 185                 190

Gly Trp Glu Gly Ser Pro Asn Asp Pro Asn Ala Gly Ser Gly Thr Met
                195                 200                 205

Gly Ala Cys Cys Ser Glu Met Asp Ile Trp Glu Ala Asn Thr Met Ala
            210                 215                 220

Ala Ala Tyr Thr Pro His Pro Cys Thr Thr Thr Gly Leu Leu Ala Cys
        225                 230                 235

Thr Gly Thr Gln Cys Gly Asp Asp Asp Asp Arg Tyr Asn Gly Val Cys
    240                 245                 250

Asp Lys Asp Gly Cys Asp Phe Asn Ser Phe Arg Met Gly Asp Lys Thr
255                 260                 265                 270

Phe Leu Gly Lys Gly Lys Thr Val Asp Thr Thr Lys Lys Ile Thr Val
                275                 280                 285

Val Thr Gln Phe Ile Thr Ser Asp Gly Thr Ala Asn Gly Asp Leu Thr
            290                 295                 300

Glu Ile Arg Arg Leu Tyr Val Gln Asn Gly Lys Val Ile Gln Asn Ser
        305                 310                 315

Met Ser Ser Ile Pro Gly Thr Thr Ala Val Asn Ser Leu Thr Asp Ala
    320                 325                 330

Ser Cys Thr Ala Gln Lys Ser Val Phe Gly Asp Thr Asn Ser Phe Ser
335                 340                 345                 350

Ser Lys Gly Gly Met Lys Ala Met Gly Asp Ser Phe Gln Arg Gly Met
                355                 360                 365

Val Leu Val Met Ser Ile Trp Asp Asp His Ala Val Asn Met Leu Trp
            370                 375                 380

Leu Asp Ser Asp Tyr Pro Thr Asp Ala Asp Pro Ser Ser Pro Gly Val
        385                 390                 395

Ala Arg Gly Glu Cys Ala Thr Thr Ser Gly Lys Pro Thr Asp Val Glu
    400                 405                 410

Ala Asn Pro Ala Gly Ile Gln Val Ile Tyr Ser Asn Ile Lys Phe Gly
415                 420                 425                 430

Asp Ile Gly Ser Thr Tyr Thr Gly Thr Ala Gly Gly Ser Pro Ser Gly
                435                 440                 445

Pro Ser Ser Thr Thr Gly Pro Ser Ser Thr Ala Ala Pro Pro Thr Asn
            450                 455                 460
```

```
Thr Ala Thr Ala Gly Leu Tyr Ala Gln Cys Gly Gly Ile Gly Phe Ser
        465                 470                 475

Gly Pro Thr Ala Cys Val Ser Gly Ala Thr Cys Thr Lys Leu Asn Asp
    480                 485                 490

Tyr Tyr Ser Gln Cys Leu Pro
495                 500


<210> SEQ ID NO 11
<211> LENGTH: 1862
<212> TYPE: DNA
<213> ORGANISM: Hohenbuehelia mastrucata
<220> FEATURE:
<221> NAME/KEY: CDS
<222> LOCATION: (1)..(190)
<220> FEATURE:
<221> NAME/KEY: sig_peptide
<222> LOCATION: (1)..(54)
<220> FEATURE:
<221> NAME/KEY: mat_peptide
<222> LOCATION: (55)..()
<220> FEATURE:
<221> NAME/KEY: Intron
<222> LOCATION: (191)..(245)
<220> FEATURE:
<221> NAME/KEY: CDS
<222> LOCATION: (246)..(586)
<220> FEATURE:
<221> NAME/KEY: Intron
<222> LOCATION: (587)..(649)
<220> FEATURE:
<221> NAME/KEY: CDS
<222> LOCATION: (650)..(721)
<220> FEATURE:
<221> NAME/KEY: Intron
<222> LOCATION: (722)..(776)
<220> FEATURE:
<221> NAME/KEY: CDS
<222> LOCATION: (777)..(1656)
<220> FEATURE:
<221> NAME/KEY: Intron
<222> LOCATION: (1657)..(1720)
<220> FEATURE:
<221> NAME/KEY: CDS
<222> LOCATION: (1721)..(1783)
<220> FEATURE:
<221> NAME/KEY: Intron
<222> LOCATION: (1784)..(1842)
<220> FEATURE:
<221> NAME/KEY: CDS
<222> LOCATION: (1843)..(1859)

<400> SEQUENCE: 11

atg ttc ccc gct tca gcc cta att gcc ctc acc ttc acc gct gtt gcc       48
Met Phe Pro Ala Ser Ala Leu Ile Ala Leu Thr Phe Thr Ala Val Ala
            -15                 -10                 -5

ttt ggc cag cag gtc ggc acc ttg aca cct gag acc cac ccg aaa ctc       96
Phe Gly Gln Gln Val Gly Thr Leu Thr Pro Glu Thr His Pro Lys Leu
    -1  1               5                   10

act gtc tcc aac tgc tca gcc ggt ggc tcg tgc aca acc agt caa cag      144
Thr Val Ser Asn Cys Ser Ala Gly Gly Ser Cys Thr Thr Ser Gln Gln
15                  20                  25                  30

tcc atc gtt ctc gat tcc aac tgg cgc tgg ctc cat tcg acc agc g        190
Ser Ile Val Leu Asp Ser Asn Trp Arg Trp Leu His Ser Thr Ser
                35                  40                  45

gtatgcacgt tgaaacgtcg attgttgttt ctttactaat tctatccgat tttag gt      247
                                                             Gly

tcg acc aac tgc tac act ggc aac acc tgg gac gcc acc ctt tgc ccg      295
Ser Thr Asn Cys Tyr Thr Gly Asn Thr Trp Asp Ala Thr Leu Cys Pro
            50                  55                  60
```

```
aac ccg aca acc tgt gcg acc aac tgc gct ctt gat ggc gcg gac tac      343
Asn Pro Thr Thr Cys Ala Thr Asn Cys Ala Leu Asp Gly Ala Asp Tyr
        65                  70                  75

tct ggc acc tac ggt atc acc act tcc ggc aat gcg ctc acc ctt aaa      391
Ser Gly Thr Tyr Gly Ile Thr Thr Ser Gly Asn Ala Leu Thr Leu Lys
    80                  85                  90

ttc gtc acc ggg aag aac gtt ggc tct cgt gtc tac ctt ctc gac agc      439
Phe Val Thr Gly Lys Asn Val Gly Ser Arg Val Tyr Leu Leu Asp Ser
95                  100                 105                 110

acg gac aac acg tac cag ttg ttc aag ctg aag aac aag gag ttc acg      487
Thr Asp Asn Thr Tyr Gln Leu Phe Lys Leu Lys Asn Lys Glu Phe Thr
                115                 120                 125

ttc gac gtc gac atg tcg aac ctt ccc tgc ggt ctc aac ggt gcc ctt      535
Phe Asp Val Asp Met Ser Asn Leu Pro Cys Gly Leu Asn Gly Ala Leu
            130                 135                 140

tac ttt tcc gag atg gct gcc aat ggc ggt ctc aac gtt ggc aac aac      583
Tyr Phe Ser Glu Met Ala Ala Asn Gly Gly Leu Asn Val Gly Asn Asn
        145                 150                 155

aag gtttgttttg catttataaa atagactgtt gttgcaaggt cctgacgagc           636
Lys

tttcgcattc cag gct ggt gcc aag tac gga act ggc tac tgc gac gct       685
               Ala Gly Ala Lys Tyr Gly Thr Gly Tyr Cys Asp Ala
               160                 165                 170

cag tgc ccg cac gac atc aag ttc atc aat ggc gag gtatgtagct           731
Gln Cys Pro His Asp Ile Lys Phe Ile Asn Gly Glu
            175                 180

tcgagaatgt agcaattatg tcctcagctc acaattaccc tccag gcc aac gtc att    788
                                                  Ala Asn Val Ile
                                                      185

aac tgg gct gga tcg ccg aac gac gtc aac gcc ggc agt ggc aag tac      836
Asn Trp Ala Gly Ser Pro Asn Asp Val Asn Ala Gly Ser Gly Lys Tyr
        190                 195                 200

gga gcc tgc tgc gac gag atg gac gtc tgg gag gcc aat aac atg gcg      884
Gly Ala Cys Cys Asp Glu Met Asp Val Trp Glu Ala Asn Asn Met Ala
    205                 210                 215

agc gcg tat act cct cac ccg tgc tcg agc act ggc ttg acc cgt tgc      932
Ser Ala Tyr Thr Pro His Pro Cys Ser Ser Thr Gly Leu Thr Arg Cys
220                 225                 230                 235

tcc gac gac gac gct acc aac aag tgt ggt gac ggc tcg aat cgc tac      980
Ser Asp Asp Asp Ala Thr Asn Lys Cys Gly Asp Gly Ser Asn Arg Tyr
                240                 245                 250

tcg agt atc tgc gac aag gac ggc tgc gac ttc aac tcg ttc cgc atg     1028
Ser Ser Ile Cys Asp Lys Asp Gly Cys Asp Phe Asn Ser Phe Arg Met
            255                 260                 265

ggc gac aag aac ttc ttc ggc aag ggt aag acg att gac act acc aag     1076
Gly Asp Lys Asn Phe Phe Gly Lys Gly Lys Thr Ile Asp Thr Thr Lys
        270                 275                 280

aag att acc gtc gtc aca cag ttc atc acc gcc gac ggc acc gac act     1124
Lys Ile Thr Val Val Thr Gln Phe Ile Thr Ala Asp Gly Thr Asp Thr
    285                 290                 295

ggt gcg ctc tcg gag atc cgt cgc atc tac ctc cag aac ggt gtc gtg     1172
Gly Ala Leu Ser Glu Ile Arg Arg Ile Tyr Leu Gln Asn Gly Val Val
300                 305                 310                 315

tac cag aac agc cag tcg acg tac tcg acc gtc cct ggc aac tcg atc     1220
Tyr Gln Asn Ser Gln Ser Thr Tyr Ser Thr Val Pro Gly Asn Ser Ile
                320                 325                 330

acc gac gcg ttc tgc gac gcg cag aag acg gcg ttc gga gac cag aac     1268
Thr Asp Ala Phe Cys Asp Ala Gln Lys Thr Ala Phe Gly Asp Gln Asn
            335                 340                 345
```

```
cgg ttc aaa gcc ctc ggc ggc atc aag gct atg ggc gac tcg atg gcc      1316
Arg Phe Lys Ala Leu Gly Gly Ile Lys Ala Met Gly Asp Ser Met Ala
        350                 355                 360

aac ggc atg gtt ctt gtc atg tcg atc tgg gac gac cat gag gcg aag      1364
Asn Gly Met Val Leu Val Met Ser Ile Trp Asp Asp His Glu Ala Lys
    365                 370                 375

atg ctc tgg ctg gac tcc aac tac ccg ctt gac aag cct gcg acg agc      1412
Met Leu Trp Leu Asp Ser Asn Tyr Pro Leu Asp Lys Pro Ala Thr Ser
380                 385                 390                 395

cct ggt gtt gct cgc ggc gag tgc gcg acc acc tcc ggc gag ccc acc      1460
Pro Gly Val Ala Arg Gly Glu Cys Ala Thr Thr Ser Gly Glu Pro Thr
                400                 405                 410

gac gta gag tcg cag gtt ccg aac tcg tcg gtg acg ttc tcg aat atc      1508
Asp Val Glu Ser Gln Val Pro Asn Ser Ser Val Thr Phe Ser Asn Ile
            415                 420                 425

aag ttc ggc ccc atc ggt agc aca tac agc ggc acg acg ggc acc ccg      1556
Lys Phe Gly Pro Ile Gly Ser Thr Tyr Ser Gly Thr Thr Gly Thr Pro
        430                 435                 440

agt agc ggc agc tcc tcc gtc atc ccg ccc agc agc tcg gtc tct aca      1604
Ser Ser Gly Ser Ser Ser Val Ile Pro Pro Ser Ser Ser Val Ser Thr
    445                 450                 455

tcg agc gcc cct tcg cag acc ggc acg gtt gct cac tgg ggc caa tgc      1652
Ser Ser Ala Pro Ser Gln Thr Gly Thr Val Ala His Trp Gly Gln Cys
460                 465                 470                 475

gga g gtaagttgtt caaatgctgt tcataaattg gcttggtctc agtctaattg        1706
Gly

ttgtcggatt caag gc  att ggc tat act ggc ccg acc acc tgc gtg gct      1755
                Gly Ile Gly Tyr Thr Gly Pro Thr Thr Cys Val Ala
                            480                 485

ccc tac act tgc caa gtc ggc aac cct t gtacgtggtc tcccctcttg          1803
Pro Tyr Thr Cys Gln Val Gly Asn Pro
    490                 495

atgatgatgc cactactgaa gagaacgtcg tctcccaag ac  tac tct cag tgc       1856
                                           Tyr Tyr Ser Gln Cys
                                                   500

ctc taa                                                              1862
Leu
```

<210> SEQ ID NO 12
<211> LENGTH: 521
<212> TYPE: PRT
<213> ORGANISM: Hohenbuehelia mastrucata

<400> SEQUENCE: 12

```
Met Phe Pro Ala Ser Ala Leu Ile Ala Leu Thr Phe Thr Ala Val Ala
            -15                 -10                 -5

Phe Gly Gln Gln Val Gly Thr Leu Thr Pro Glu Thr His Pro Lys Leu
    -1  1               5                   10

Thr Val Ser Asn Cys Ser Ala Gly Gly Ser Cys Thr Thr Ser Gln Gln
15                  20                  25                  30

Ser Ile Val Leu Asp Ser Asn Trp Arg Trp Leu His Ser Thr Ser Gly
                35                  40                  45

Ser Thr Asn Cys Tyr Thr Gly Asn Thr Trp Asp Ala Thr Leu Cys Pro
            50                  55                  60

Asn Pro Thr Thr Cys Ala Thr Asn Cys Ala Leu Asp Gly Ala Asp Tyr
        65                  70                  75

Ser Gly Thr Tyr Gly Ile Thr Thr Ser Gly Asn Ala Leu Thr Leu Lys
    80                  85                  90
```

```
Phe Val Thr Gly Lys Asn Val Gly Ser Arg Val Tyr Leu Leu Asp Ser
95                  100                 105                 110

Thr Asp Asn Thr Tyr Gln Leu Phe Lys Leu Lys Asn Lys Glu Phe Thr
                115                 120                 125

Phe Asp Val Asp Met Ser Asn Leu Pro Cys Gly Leu Asn Gly Ala Leu
            130                 135                 140

Tyr Phe Ser Glu Met Ala Ala Asn Gly Gly Leu Asn Val Gly Asn Asn
        145                 150                 155

Lys Ala Gly Ala Lys Tyr Gly Thr Gly Tyr Cys Asp Ala Gln Cys Pro
    160                 165                 170

His Asp Ile Lys Phe Ile Asn Gly Glu Ala Asn Val Ile Asn Trp Ala
175                 180                 185                 190

Gly Ser Pro Asn Asp Val Asn Ala Gly Ser Gly Lys Tyr Gly Ala Cys
                195                 200                 205

Cys Asp Glu Met Asp Val Trp Glu Ala Asn Asn Met Ala Ser Ala Tyr
            210                 215                 220

Thr Pro His Pro Cys Ser Ser Thr Gly Leu Thr Arg Cys Ser Asp Asp
        225                 230                 235

Asp Ala Thr Asn Lys Cys Gly Asp Gly Ser Asn Arg Tyr Ser Ser Ile
    240                 245                 250

Cys Asp Lys Asp Gly Cys Asp Phe Asn Ser Phe Arg Met Gly Asp Lys
255                 260                 265                 270

Asn Phe Phe Gly Lys Gly Lys Thr Ile Asp Thr Thr Lys Lys Ile Thr
                275                 280                 285

Val Val Thr Gln Phe Ile Thr Ala Asp Gly Thr Asp Thr Gly Ala Leu
            290                 295                 300

Ser Glu Ile Arg Arg Ile Tyr Leu Gln Asn Gly Val Val Tyr Gln Asn
        305                 310                 315

Ser Gln Ser Thr Tyr Ser Thr Val Pro Gly Asn Ser Ile Thr Asp Ala
    320                 325                 330

Phe Cys Asp Ala Gln Lys Thr Ala Phe Gly Asp Gln Asn Arg Phe Lys
335                 340                 345                 350

Ala Leu Gly Gly Ile Lys Ala Met Gly Asp Ser Met Ala Asn Gly Met
                355                 360                 365

Val Leu Val Met Ser Ile Trp Asp Asp His Glu Ala Lys Met Leu Trp
            370                 375                 380

Leu Asp Ser Asn Tyr Pro Leu Asp Lys Pro Ala Thr Ser Pro Gly Val
        385                 390                 395

Ala Arg Gly Glu Cys Ala Thr Thr Ser Gly Glu Pro Thr Asp Val Glu
    400                 405                 410

Ser Gln Val Pro Asn Ser Ser Val Thr Phe Ser Asn Ile Lys Phe Gly
415                 420                 425                 430

Pro Ile Gly Ser Thr Tyr Ser Gly Thr Thr Gly Thr Pro Ser Ser Gly
                435                 440                 445

Ser Ser Ser Val Ile Pro Pro Ser Ser Ser Val Ser Thr Ser Ser Ala
            450                 455                 460

Pro Ser Gln Thr Gly Thr Val Ala His Trp Gly Gln Cys Gly Gly Ile
        465                 470                 475

Gly Tyr Thr Gly Pro Thr Thr Cys Val Ala Pro Tyr Thr Cys Gln Val
    480                 485                 490

Gly Asn Pro Tyr Tyr Ser Gln Cys Leu
495                 500
```